United States Patent [19]

Yoshikumi et al.

[11] Patent Number: 4,663,438

[45] Date of Patent: May 5, 1987

[54] NOVEL NUCLEIC ACID-CONTAINING GLYCOPROTEIN

[75] Inventors: Chikao Yoshikumi, Kunitachi; Takayoshi Fujii, Tokyo; Takao Furusho, Machida; Kenichi Matsunaga, Tokorozawa; Minoru Ohara; Akira Kobayashi, both of Tokyo, all of Japan

[73] Assignee: Kureha Kagaku Kogyo Kabushiki Kaisha, Tokyo, Japan

[21] Appl. No.: 715,816

[22] Filed: Mar. 25, 1985

Related U.S. Application Data

[63] Continuation-in-part of Ser. No. 343,834, Jan. 29, 1982, abandoned.

[30] Foreign Application Priority Data

Feb. 10, 1981 [JP] Japan .................................. 56-18655

[51] Int. Cl.$^4$ ............................................ C07K 15/14
[52] U.S. Cl. .................................................. 530/395
[58] Field of Search .................... 260/112 R; 424/115; 536/18.7; 530/395

[56] References Cited

U.S. PATENT DOCUMENTS

| | | | |
|---|---|---|---|
| 4,188,384 | 2/1980 | Yoshikumi et al. | 424/180 |
| 4,202,885 | 5/1980 | Asano et al. | 424/95 |
| 4,202,969 | 5/1980 | Ueno et al. | 536/1 |
| 4,228,275 | 10/1980 | Asano et al. | 424/115 |
| 4,243,662 | 1/1981 | Asano et al. | 536/18.7 |
| 4,271,151 | 6/1981 | Hotta et al. | 260/112 R |
| 4,289,688 | 9/1981 | Hotta et al. | 260/112 R |

*Primary Examiner*—Delbert R. Phillips
*Attorney, Agent, or Firm*—Wegner & Bretschneider

[57] ABSTRACT

Disclosed herein is a nucleic acid-containing glycoprotein having molecular weight of 5,000 to 300,000 as determined by ultracentrifugal method; the weight ratio of protein moiety thereof determined by Lowry-Folin's method to saccharide moiety thereof determined by phenol-sulfuric acid method of in the range of 50/50 to 80/20; N-terminal amino acid thereof consisting essentially of tyrosine, leucine or alanine; leucine-phenylalanine-valine as amino acid sequence at C-terminal thereof; the elementary composition consisting essentially of 35.2 to 49.3% of C, 4.8 to 8.0% of H, 4.3 to 12.3% of N, trace to 2.5% of S, trace to 1.2% of P and the balance of O; the isoelectric point of in the range of pH 2.5 to 5.0; and nucleic acid as a component.

5 Claims, 20 Drawing Figures

NOVEL NUCLEIC ACID-CONTAINING GLYCOPROTEIN

CROSS-REFERENCE TO RELATED APPLICATION

This application is a continuation-in-part of U.S. patent application, Ser. No. 343,834 filed Jan. 29, 1982, now abandoned.

BACKGROUND OF THE INVENTION

The present invention relates to a novel nucleic acid-containing glycoprotein having an activity for inhibiting the growth of malignant tumor cells and a lectin-like activity.

The term "lectin-like activity" herein mentioned is used for describing generally cancer cell-specific cell-agglutinating activity and blast-transforming activity to lymphocytes, all of which are inherent in substances referred to as lecitin, and non-specific inhibitory function on antigen-specific erythrocyte agglutination, affinity to the surface of lymphocyte and activity to macrophage.

Formerly, the present inventors prepared a substance having an activity for inhibiting the growth of malignant tumor cells by extracting a basidiomycetous fungus belonging to the genus Coriolus with hot water or an aqueous alkali solution, and after isolating a nitrogen-containing polysaccharide from the extract, they confirmed that the nitrogen-containing polysaccharide is an active ingredient of the substance (refer to U.S. Pat. Nos. 4,051,314 and 4,202,969).

As a result of studying further the constituents of the substance extracted from the fungus, the present inventors have found a novel nucleic acid-containing glycoprotein having a higher weight ratio of the protein moiety thereof to the saccharide moiety thereof and a specific mode of bonding between the saccharide moiety and the protein moiety, and showing lectin-like physiological activities as well as an activity for inhibiting the growth of malignant tumor cells in mammals. And, the present inventors have found a novel nucleic acid-containing glycoprotein being quite different from the conventional nitrogen-containing polysaccharides and have attained the present invention.

SUMMARY OF THE INVENTION

In a first aspect of the present invention, there is provided a nucleic acid-containing glycoprotein having a molecular weight of from 5,000 to 300,000 as determined by the ultracentrifugation method; the ratio of the weight of its protein moiety, as determined by Lowry-Folin's method, to the weight of its saccharide moiety, as determined by the phenolsulfuric acid method, being from 50:50 to 80:20; the saccharide moiety containing fucose, ribose, arabinose, xylose, mannose, galactose, glucose and glucosamine, and the total weight of said xylose, said mannose and said glucose being more than 85% by weight of the total weight of said saccharides; the protein moiety containing aspartic acid, threonine, serine, glutamic acid, proline, glycine, alanine, cysteine, valine, methionine, cystathionine, isoleucine, leucine, tyrosine, phenylalanine, tryptophan, ornithine, lysine, histidine and arginine, and the total weight of said aspartic acid, said threonine, said serine, said glutamic acid, said glycine, said alanine, said phenylalanine, said valine, said leucine and said isoleucine being more than 75% by weight of the total weight of all of said amino acids; the amino acid at its N-end being tyrosine, leucine or alanine; the amino acid sequence at its C-end being leucine to phenylalanine to valine, the terminal amino acid being leucine; its elementary composition being from 35.2 to 49.3% of C, from 4.8 to 8.0% of H, from 4.3 to 12.3% of N, from a trace amount to 2.5% of S, from a trace amount to 1.2% of P and the balance being O; isoelectric point being from pH 2.5 to pH 5.0; nucleic acid containing 0.01 to 0.50% by weight of uracil as a base of nucleic acid; and the nucleic acid-containing glycoprotein showing infrared absorption maxima at $3600-3200$ cm$^{-1}$, $1530$ cm$^{-1}$ and $1200-1000^{-1}$.

In a second aspect of the present invention, there is provided a process for producing a nucleic acid-containing glycoprotein comprising the steps of extracting fruit bodies, mycelia or cultured mycelia of a basidiomycetous fungus belonging to the genus Coriolus with hot water or an aqueous 0.01 to 2.0N alkali solution at a temperature of 80° to 100° C. for 1 to 8 hours, neutralizing the obtained extract, subjecting the neutralized extract to dialysis and/or ultra-filtration thereby removing a low molecular weight substance having a molecular weight of below 5,000, and fractionally collecting the fractions precipitating under the conditions of the pH of 2.5 to 5.0, of the ion strength of 0.1 to 3.1μ at a temperature of 5° to 25° C.

In a third aspect of the present invention, there is provided a pharmaceutical composition in dosage unit form comprising as an active ingredient an effective amount of a nucleic acid-containing glycoprotein having a molecular weight of 5,000 to 300,000 as determined by the ultracentrifugation method; the ratio of the weight of its protein moiety, as determined by Lowry-Folin's method, to the weight of its saccharide moiety, as determined by the phenolsulfuric acid method, being from 50:50 to 80:20; the saccharide moiety containing fucose, ribose, arabinose, xylose, mannose, galactose, glucose and glucosamine, and the total weight of said xylose, said mannose and said glucose being more than 85% by weight of the total weight of said saccharides; the protein moiety containing aspartic acid, threonine, serine, glutamic acid, proline, glycine, alanine, cysteine, valine, methionine, cystathionine, isoleucine, leucine, tyrosine, phenylalanine, tryptophan, ornithine, lysine, histidine and arginine, and the total weight of said aspartic acid, said threonine, said serine, said glutamic acid, said glycine, said alanine, said phenylalanine, said valine, said leucine and said isoleucine being more than 75% by weight of the total weight of all of said amino acids; the amino acid at its N-end being tyrosine, leucine or alanine; the amino acid sequence at its C-end being leucine to phenylalanine to valine, the terminal amino acid being leucine; its elementary composition being from 35.2 to 49.3% of C, from 4.8 to 8.0% of H, from 4.3 to 12.3% of N, from a trace amount to 2.5% of S, from a trace amount to 1.2% of P and the balance being O; isoelectric point being from pH 2.5 to pH 5.0; nucleic acid containing 0.01 to 0.50% by weight of uracil as a base of nucleic acid; and nucleic acid-containing glycoprotein showing infrared absorption maxima at $3600-3200$ cm$^{-1}$, $1530$ cm$^{-1}$ and $1200-1000$ cm$^{-1}$; effective for inhibiting the growth of the tumor cells, and a carrier therefor.

In a fourth aspect of the present invention, there is provided a method for inhibiting the growth of malignant tumor cells in humans which comprises administering to a patient suffering from the malignant tumor an effective amount of a nucleic acid-containing glycoprotein having a molecular weight of from 5,000 to 300,000 as determined by the ultracentrifugation method; the ratio of the weight of its protein moiety, as determined by Lowry-Folin's method, to the weight of its saccharide moiety, as determined by the phenolsulfuric acid method, being from 50:50 to 80:20; the saccharide moiety containing fucose, ribose, arabinose, xylose, mannose, galactose, glucose and glucosamine, and the total weight of said xylose, said mannose and said glucose being more than 85% by weight of the total weight of said saccharides; the protein moiety containing aspartic acid, threonine, serine, glutamic acid, proline, glycine, alanine, cysteine, valine, methionine, cystathionine, isoleucine, leucine, tyrosine, phenylalanine, tryptophan, ornithine, lysine, histidine and arginine, and the total weight of said aspartic acid, said threonine, said serine, said glutamic acid, said glycine, said alanine, said phenylalanine, said valine, said leucine and said isoleucine being more than 75% by weight of the total weight of all of said amino acids; the amino acid at its N-end being tyrosine, leucine or alanine; the amino acid sequence at its C-end being leucine to phenylalanine to valine, the terminal amino acid being leucine; its elementary composition being from 35.2 to 49 3% of C, from 4.8 to 8.0% of H, from 4.3 to 12.3% of N, from a trace amount to 2.5% of S, from a trace amount to 1.2% of P and the balance being 0; isoelectric point being from pH 2.5 to pH 5.0; nucleic acid containing 0.01 to 0.50% by weight of uracil as a base of nucleic acid; and the nucleic acid-containing glycoprotein showing infrared absorption maxima at $3600-3200$ cm$^{-1}$, $1530$ cm$^{-1}$ and $1200-1000^{-1}$.

DETAILED DESCRIPTION OF THE INVENTION

Figure 1:
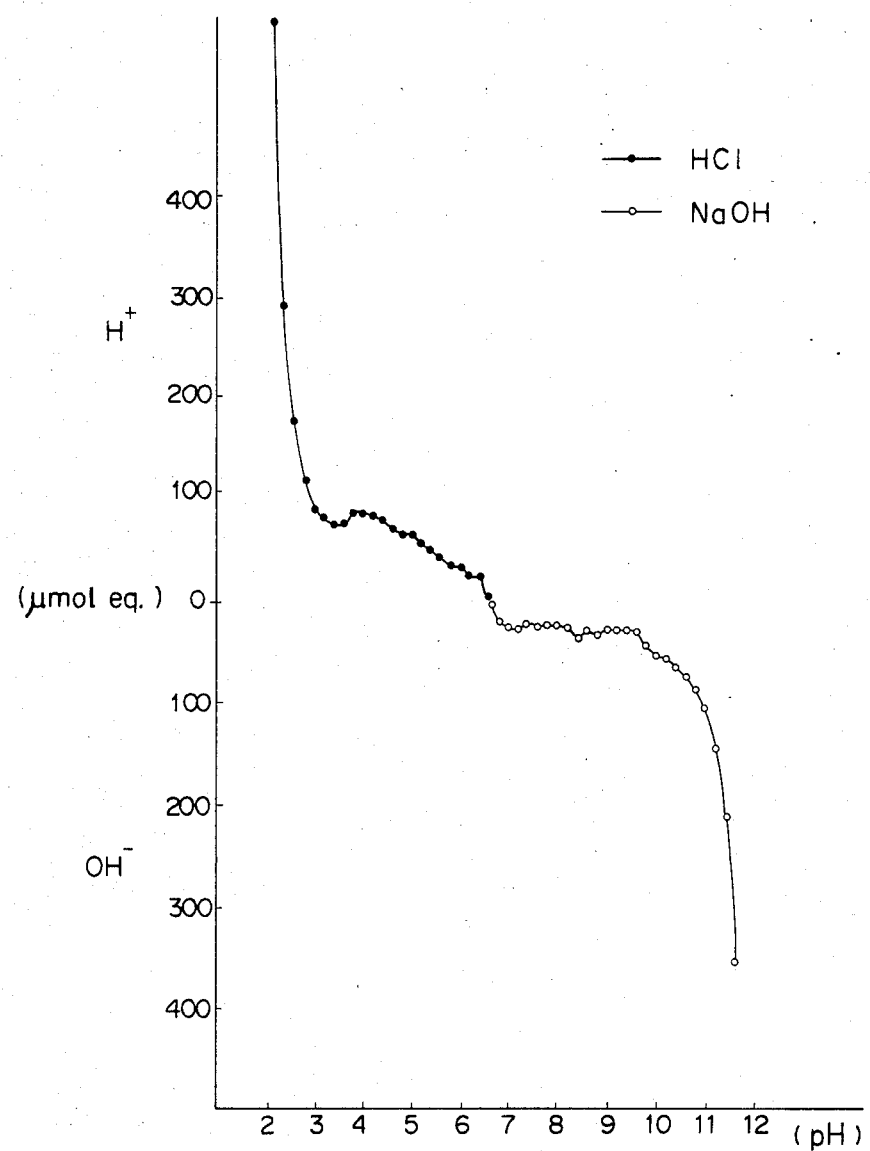
FIG. 1 shows the titration curve (concentration of both H+ and OH− vs. pH of the solution of the present substance) of the nucleic acid-containing glycoprotein according to the present invention with aqueous 0.02N hydrochloric acid solution and aqueous 0.02 N sodium hydroxide solution.
Figure 2:
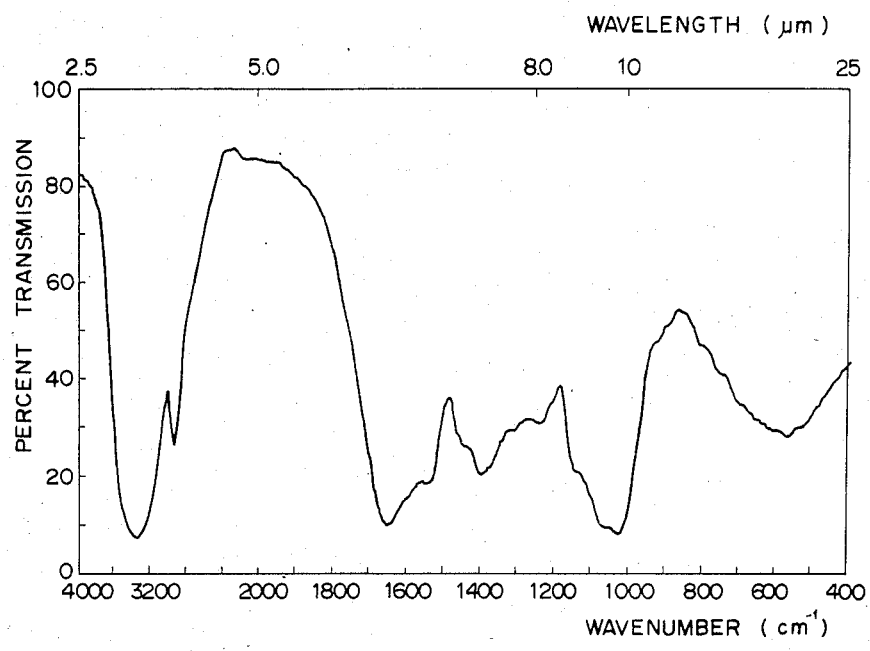
FIGS. 2-19 show the respective infrared absorption spectra of the glycoprotein according to the present invention (Examples 1-18) and FIG. 20 shows the chemotaxis of macrophages to the nucleic acid-containing glycoprotein according to the present invention, based on the results of determination of the number of exuded cells vs. the concentration of the present substance into the peritoneal cavity by a hemocytemeter.
Figure 3:
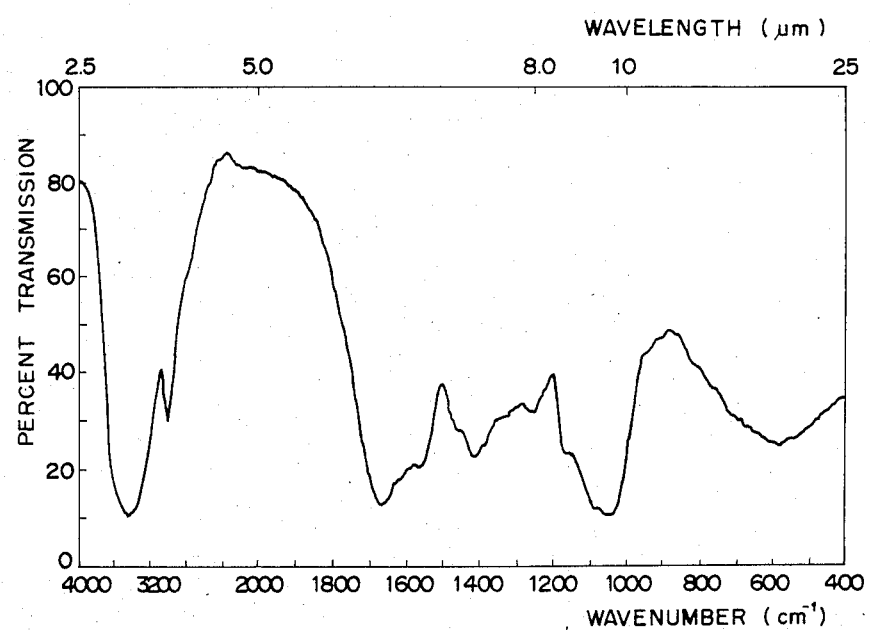
Figure 4:
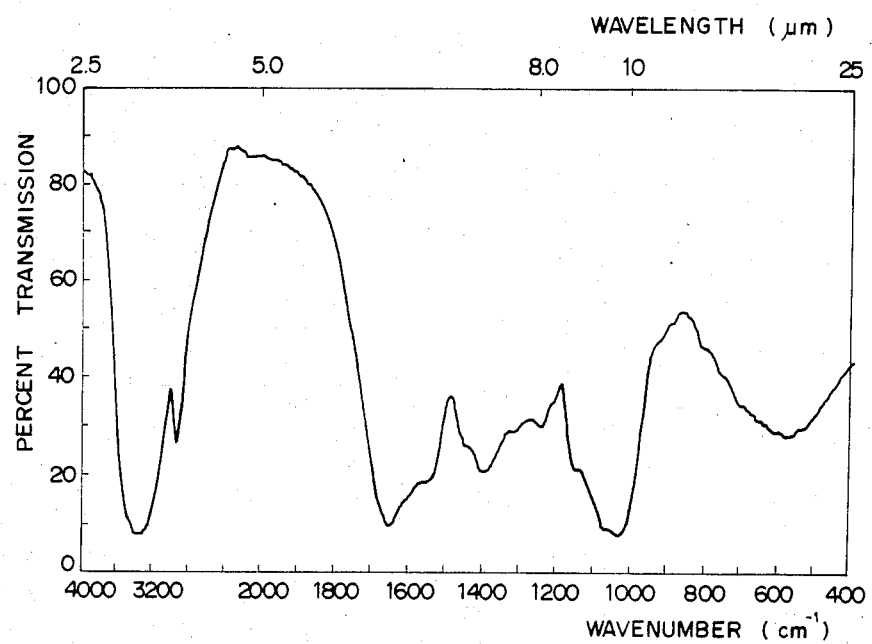
Figure 5:
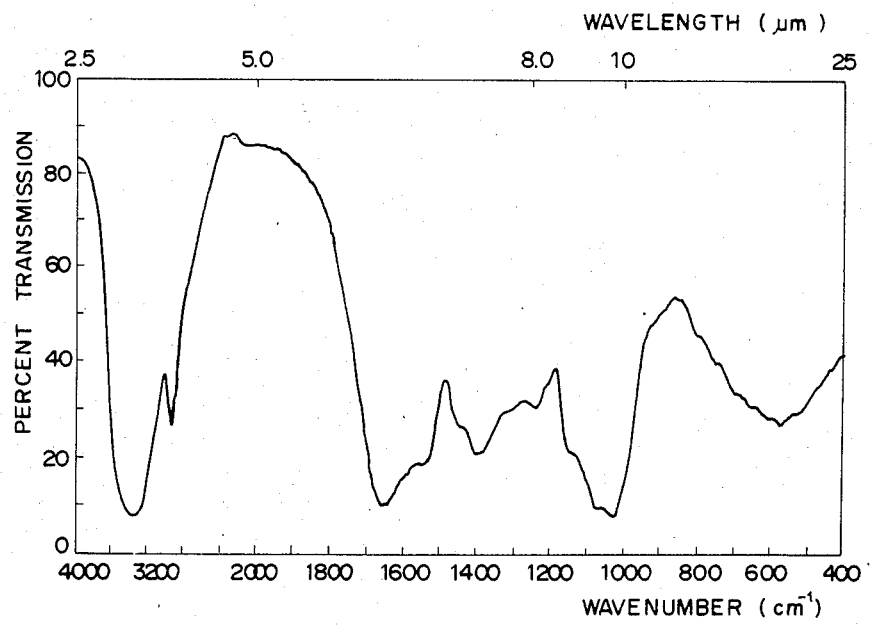
Figure 6:
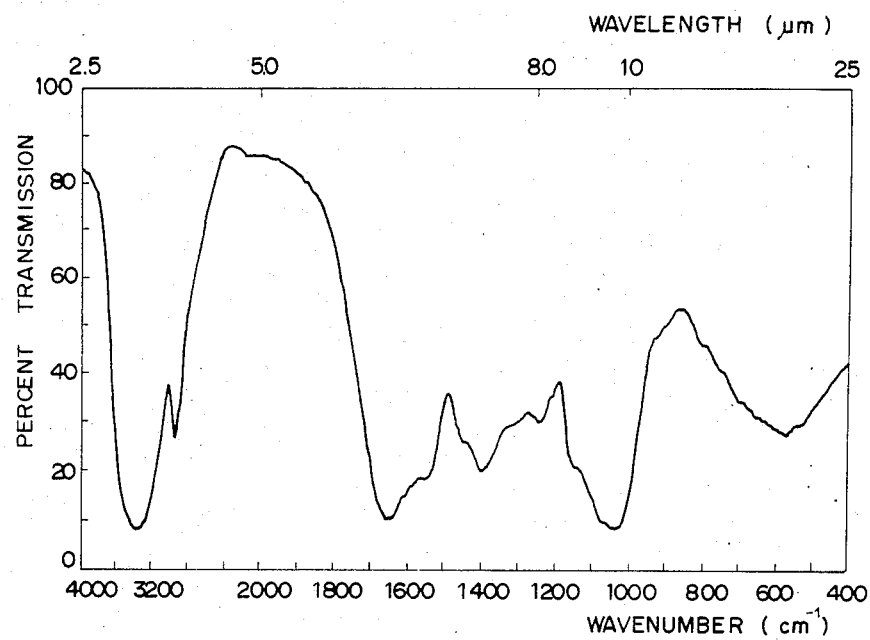
Figure 7:
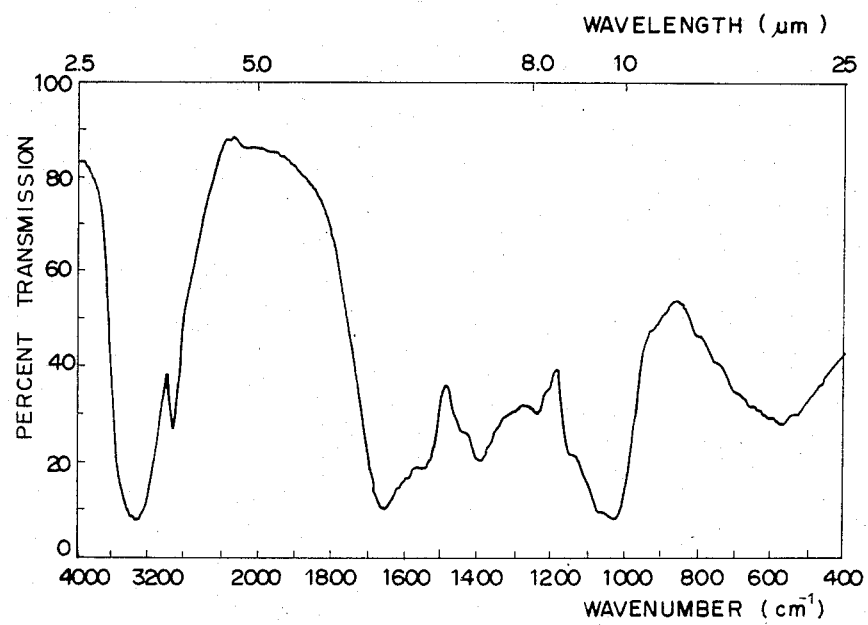
Figure 8:
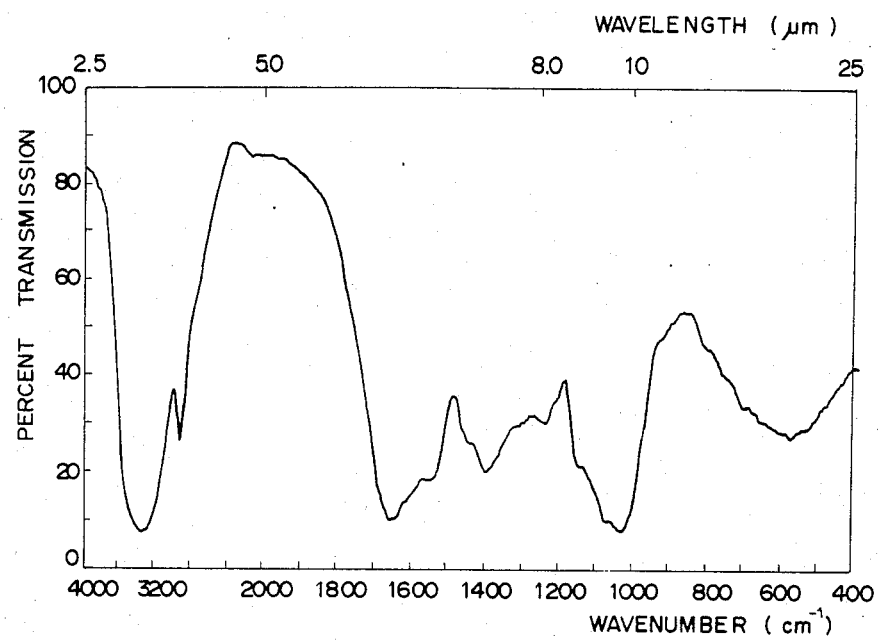
Figure 9:
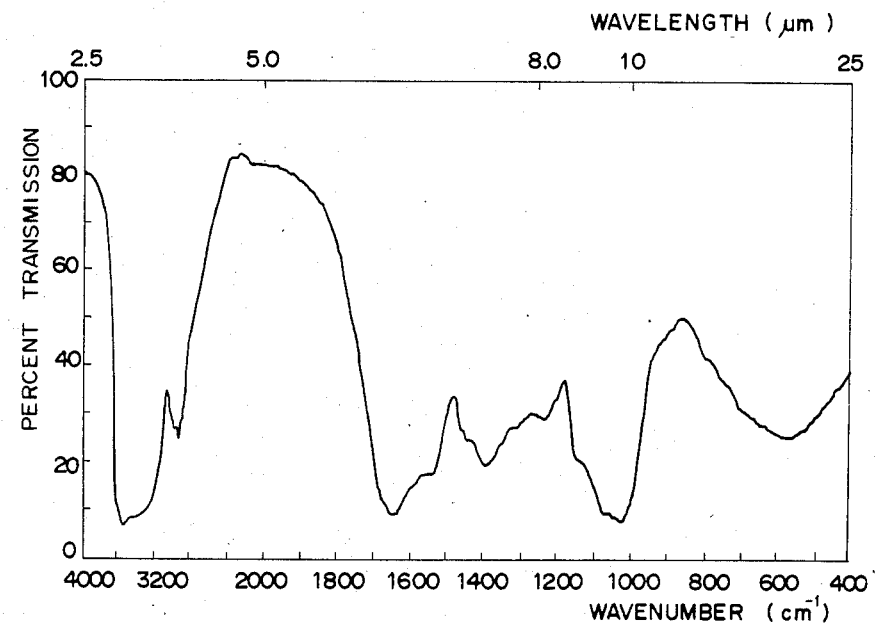
Figure 10:
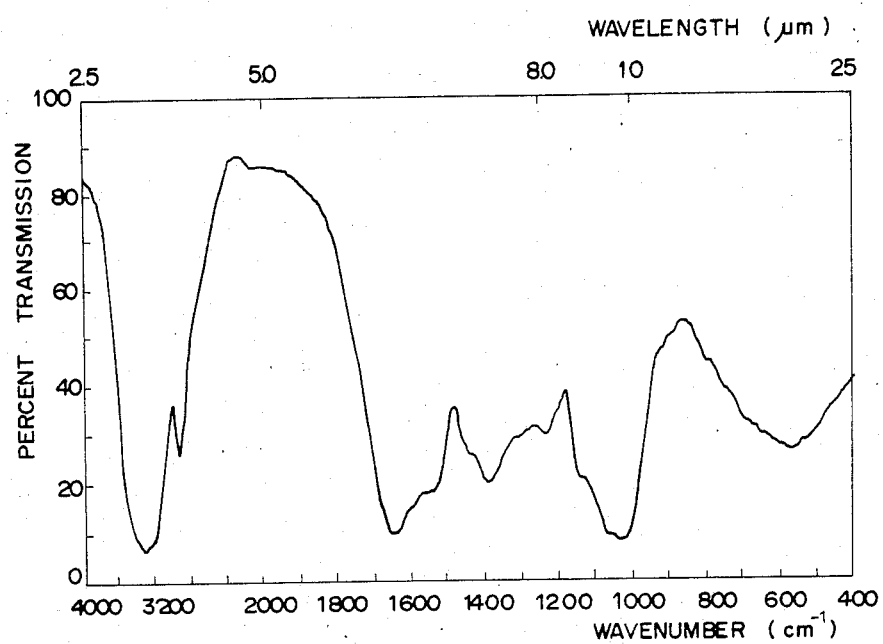
Figure 11:
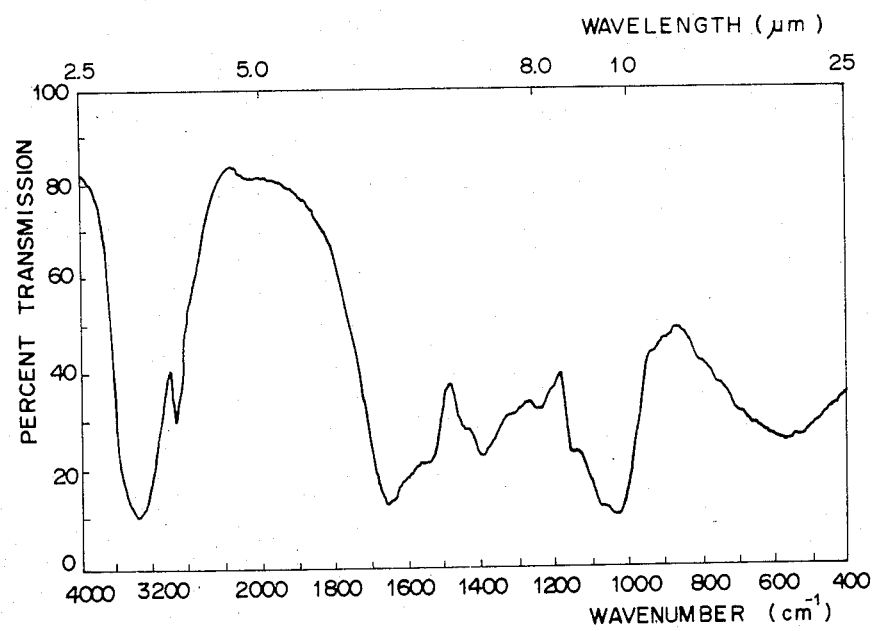
Figure 12:
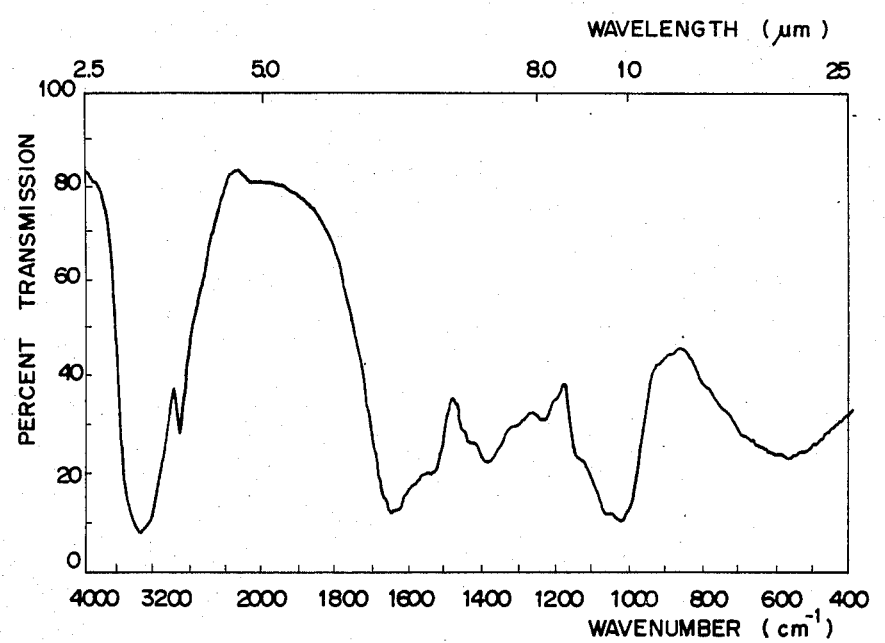
Figure 13:
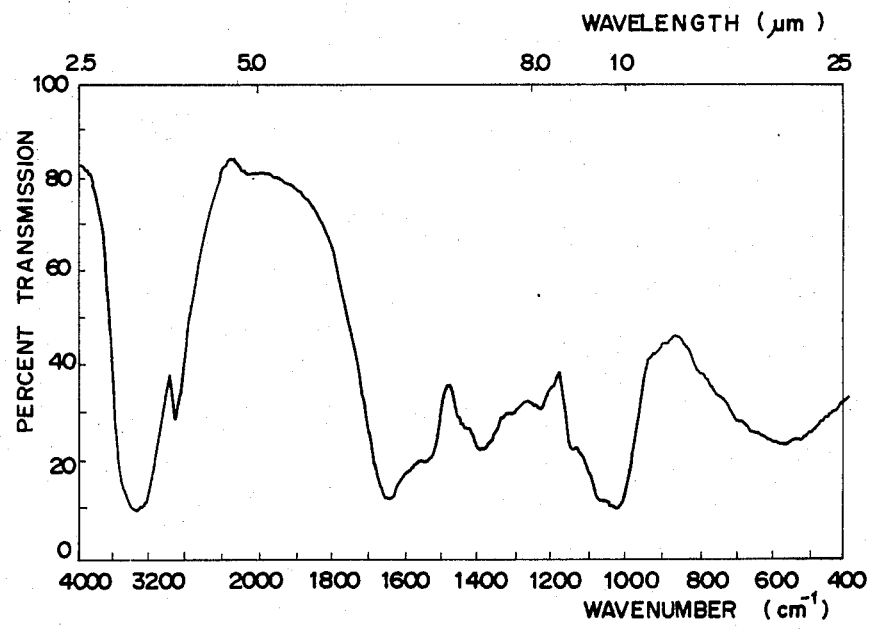
Figure 14:
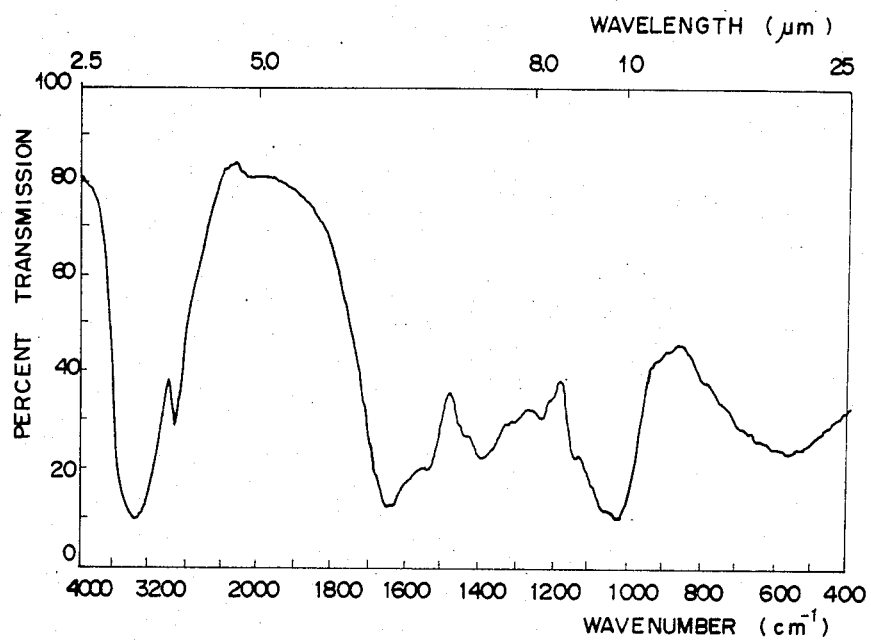
Figure 15:
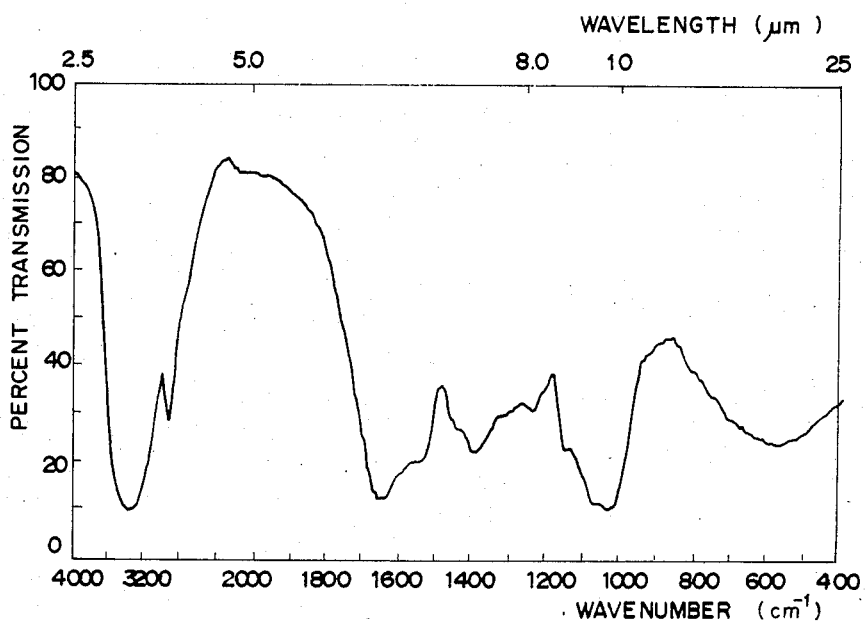
Figure 16:
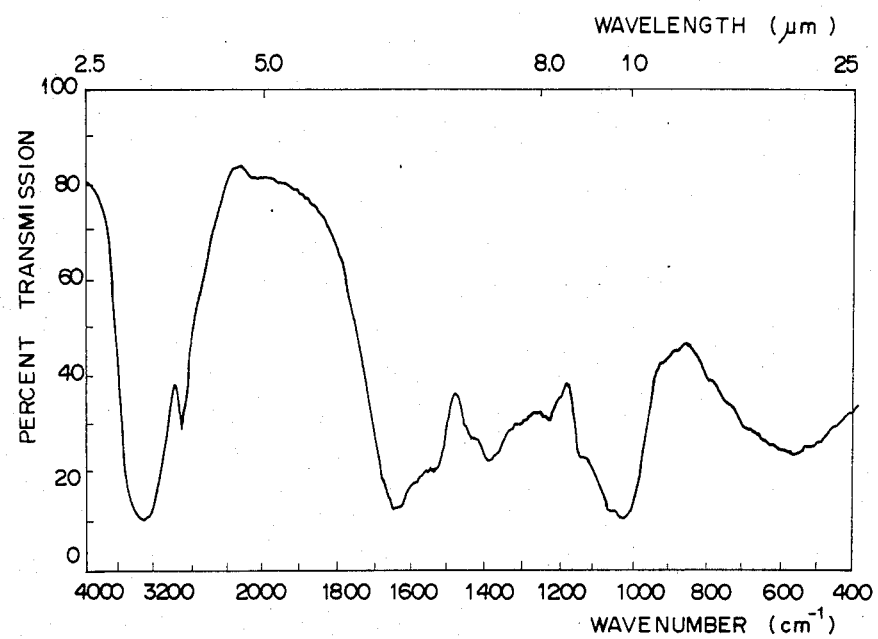
Figure 17:
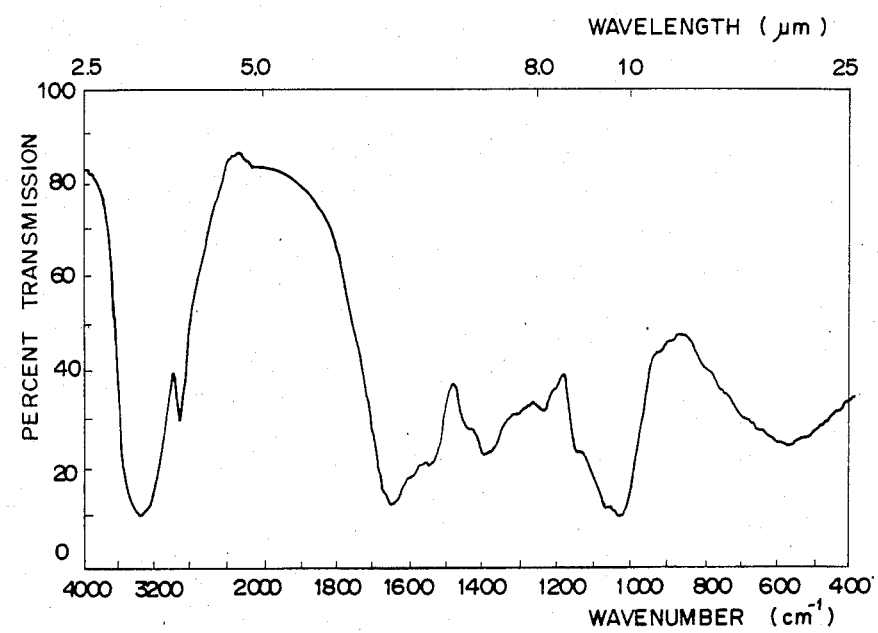
Figure 18:
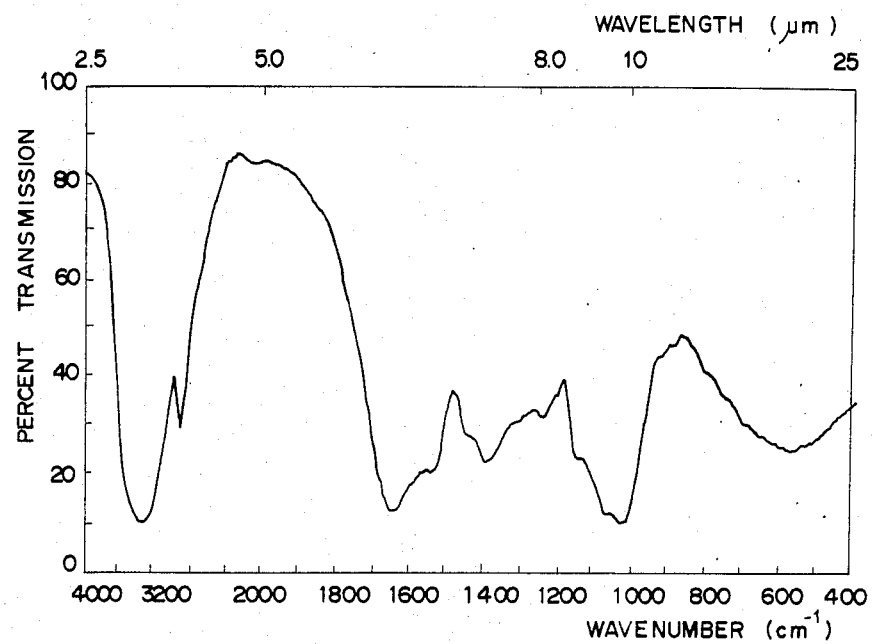
Figure 19:
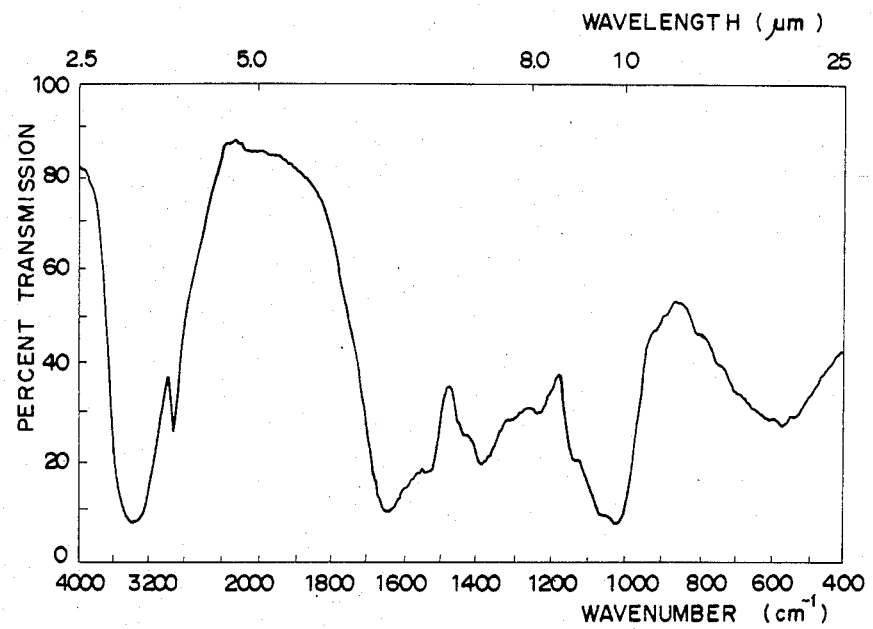

The novel glycoprotein according to the present invention can be characterized and specified generically as follows:

(1) the molecular weight is in a range of 5,000 to 300,000 as determined by the method of ultracentrifugation,
(2) the weight ratio of the protein moiety thereof determined by Lowry-Folin's method to the weight of the saccharide moiety thereof determined by phenol-sulfuric acid method is in a range of 50/50 to 80/20.
(3) the amino acid occupying the N-terminal of the protein moiety thereof consists essentially of tyrosine, leucin or alanine,
(4) the amino acid sequence from the c-terminal of protein moiety thereof is in the order of leucine to phenylalanine to valine,
(5) the elementary composition consists essentially of 35.2 to 49.3% of C, 4.8 to 8.0% of H, 4.3 to 12.3 of N, trace to 2.5 of S, trace to 1.2% of P and the balance of O,
(6) the isoelectric point is 2.5 to 5.0 in pH and
(7) nucleic acid is contained as a component.

The novel nucleic acid-containing glycoprotein of the present invention (hereinafter refer to as the "present substance") is prepared by the following process:

Fruit bodies, mycelia or artificially cultured mycelia of a basidiomycetous fungus, for example, Coriolus versicolor (Fr.) Quél., Coriolus hirsutus (Fr.) Quél., Coriolus pargamenus (Fr.) Pat., Coriolus consors (Fr.) Quél. and Coriolus conchifer (Schw.) Pat. are extracted, as the starting material, with an aqueous solvent such as hot water or aqueous 0.01 to 2.0N alkali solution at a temperature of 80° to 100° C. for 1 to 8 hours. After removing the extraction residue, the aqueous extract is neutralized with an acid and condensed. After desalting the condensate, if necessary, the condensate is subjected to dialysis and/or ultrafiltration to remove the low molecular weight substance having a molecular weight of below 5,000. The thus obtained product is condensed and dried to be a powdery substance, if necessary. Then, the product or the powdery substance is treated with a method of fractional precipitation at isoelectric point under the conditions of the pH of 2.5 to 5.0, of the ion strength of 0.1 to 3.1μ at a temperature of 5° to 25° C. of the medium containing the product or the powdery substance, for more than 0.5 hours.

In addition, the artificially cultured mycelia are obtained by the procedures of culturing each of the basidiomycetous fungi in a culture medium, homogenizing the thus proliferated mycelia on the culture medium in the presence of an aqueous physiological saline solution and inoculating the thus homogenized culture medium containing the mycelium as a seed culture into stationary culture medium or submerged culture medium. From the view point of productivity, the use of artificially cultured myeclia is preferable.

Of the basidiomycetous fungi used in the process of the present invention, those deposited are shown in Table 1, and of those deposited, it is profitable from the view point of productivity to use the strain CM-101 of Coriolus versicolor (Fr.) Quél. (FERM-P 2412).

TABLE 1

| Species | Strain | Deposition Number of the Strain |
|---|---|---|
| Coriolus versicolor (Fr.) Quel. | CM-101 | FERM-P 2412 (ATCC 20547) |
| Coriolus versicolor (Fr.) Quel. | CM-102 | FERM-P 2413 (ATCC 20548) |
| Coriolus versicolor (Fr.) Quel. | CM-103 | FERM-P 2414 (ATCC 20545) |
| Coriolus versicolor (Fr.) Quel. | CM-104 | FERM-P 2415 (ATCC 20549) |
| Coriolus versicolor (Fr.) Quel. | CM-105 | FERM-P 2416 (ATCC 20550) |
| Coriolus versicolor (Fr.) Quel. | CM-106 | FERM-P 2417 (ATCC 20551) |
| Coriolus versicolor (Fr.) Quel. | CM-107 | FERM-P 2418 (ATCC 20552) |
| Coriolus versicolor (Fr.) Quel. | CM-108 | FERM-P 2419 (ATCC 20553) |
| Coriolus versicolor (Fr.) Quel. | CM-109 | FERM-P 2420 (ATCC 20554) |
| Coriolus versicolor (Fr.) Quel. | CM-110 | FERM-P 2421 (ATCC 20555) |

TABLE 1-continued

| Species | Strain | Deposition Number of the Strain |
|---|---|---|
| Coriolus versicolor (Fr.) Quel. | CM-111 | FERM-P 2422 (ATCC 20556) |
| Coriolus versicolor (Fr.) Quel. | CM-112 | FERM-P 2423 (ATCC 20557) |
| Coriolus versicolor (Fr.) Quel. | CM-113 | FERM-P 2424 (ATCC 20558) |
| Coriolus versicolor (Fr.) Quel. | CM-114 | FERM-P 2425 (ATCC 20559) |
| Coriolus versicolor (Fr.) Quel. | CM-115 | FERM-P 2426 (ATCC 20560) |
| Coriolus hirsutus (Fr.) Quel. | CM-151 | FERM-P 2711 (ATCC 20561) |
| Coriolus pargamenus (Fr.) Pat. | CM-161 | FERM-P 2712 (ATCC 20562) |
| Coriolus versicolor (Fr.) Quel. | GX-101-3 | FERM-P 3686 (ATCC 20564) |
| Coriolus consors (Berk.) Imaz. | CM-166 | FERM-P 988 (ATCC 20565) |

(Note)
FERM: Fermentation Research Institute, Agency of Industrial Science and Technology (Japan)
ATCC: American Type Culture Collection (U.S.A.)

The properties characterizing and specifying the thus obtained substance according to the present invention, are more precisely described as follows:

(1) Molecular weight: 5,000 to 300,000.

In the present invention, the value of molecular weight was obtained by the determination on the method of ultracentrifugation generally for use in determining molecular weight of highmolecular substances.

(2) Colour reaction:

The presence of protein structure in the present substance was confirmed by the blue colouring in Lowry-Folin's reaction, and by the purplish blue colouring in ninhydrine reaction on the hydrolyzate of the present substance with hydrochloric acid.

The presence of saccharide structure in the present substance was confirmed by purple colouring in α-naphthol-sulfuric acid reaction, brown colouring in indole-sulfuric acid reaction, green colouring in anthrone-sulfuric acid reaction, purplish brown colouring in tryptophan-sulfuric acid reaction, greenish brown colouring both in thioglycolic acid-sulfuric acid reaction and in orcine-hydrochloric acid reaction.

(3) Weight ratio of the protein moiety to the saccharide moiety thereof: 50/50 to 80/20.

The respective contents of the protein moiety and the saccharide moiety of the present substance were quantitatively determined by Lowry-Folin's method and phenol-sulfuric acid method, and the weight ratio of both the two moieties was calculated from the contents. In addition, in consideration of the fact of not observing any formation of precipitates both in Sevag's test method and trifluoromethane test method, it was confirmed that the protein moiety and the saccharide moiety of the present substance are in chemical bonding.

(4) The mode of bonding between the saccharide- and protein moieties:

Concerning the mode of bonding between the saccharide moiety and the protein moiety of the present substance, among the generally known modes of bonding between saccharide and protein such as N-acylglycosylamine type, C-glycoside type and glycoside ester type, etc., it was presumed that N-acylglycosylamine type was predominant in the present substance because of the difficulty in breaking the bonding by weak alkali and of the confirmation of glucosamine on amino acid analysis of the hydrolyzate of the present substance.

(5) Composition of amino acids in the protein moiety:

The composition of amino acids in the protein moiety of the present substance determined by the conventional method is shown in Table 2:

TABLE 2

| Amino acid | Content in % by weight |
|---|---|
| Aspartic acid | 10 to 20 |
| Threonine | 4 to 6 |
| Serine | 3 to 6 |
| Glutamic acid | 10 to 16 |
| Proline | trace to 8 |
| Glycine | 6 to 10 |
| Alanine | 6 to 13 |
| Cystine | trace |
| Valine | 5 to 12 |
| Methionine | trace to 4 |
| Cystathionine | trace to 3 |
| Isoleucine | 3 to 8 |
| Leucine | 8 to 13 |
| Tyrosine | trace to 5 |
| Phenylalanine | 3 to 9 |
| Tryptophan | trace to 1 |
| Ornithine | trace to 2 |
| Lysine | 1 to 4 |
| Histidine | tract to 2 |
| Arginine | 1 to 4 |
| (Ammonia) | (1 to 7) |

As is seen in Table 2, of these amino acids, the total sum of the amounts of aspartic acid, threonine, serine, glutamic acid, phenylalanine, isoleucine, glycine, alanine, valine and leucine occupies more than 75% by weight of the total amino acids.

(6) The kinds of amino acid at N-terminal of the protein moiety and the amino acid sequence from C-terminal of the protein moiety:

The kinds of N-terminal amino acid of the protein moiety of the present substance were determined by the conventional method in which the amino group in the terminal amino acid residue was dinitrophenylated, and after hydrolyzing the product by an acid, the thus formed dinitrophenylamino acid was identified by thin-layer chromatography and high speed-liquid chromatography to be tyrosine, leucine or alanine.

The amino acid sequence from the C-terminal of the protein moiety of the present invention was determined by the method using carboxypeptidase, in which the amino acids obtained by hydrolyzing the present substance with carboxypeptidase were analyzed by thin-layer chromatography to be in the order of leucine-phenylalanine-valine.

(7) Isoelectric point of the present substance: pH 2.5 to 5.0.

In order to examine the physical specificity of the protein moiety of the present substance, the present substance was subjected to electrophoresis using the column ampholine method. In consideration of the isoelectric point of the present substance in a range of pH 2.5 to 5.0, it was confirmed that the present substance is an acidic glycoprotein complex. In this connection, the titration curve of the present substance is as is seen in FIG. 1, wherein the curve is the result of titrating an aqueous 1% by weight solution of the present substance with aqueous 0.02N hydrochloric acid solution and aqueous 0.02N sulfuric acid solution.

(8) Constitution of the saccharide moiety of the present substance:

The constitution of the saccharide moiety of the present substance was confirmed following the ordinary method by which the hydrolyzate of the present substance was reduced and then acetylated, and the product was subjected to gas chromatographic analysis. The result is shown in Table 3.

TABLE 3

| (Mono) saccharide | % by weight |
|---|---|
| Fucose | 0.5 to 4.0 |
| Ribose | trace to 2.0 |
| Arabinose | 0.3 to 6.0 |
| Xylose | 2.0 to 40.0 |
| Mannose | 5.0 to 20.0 |
| Galactose | 0.5 to 8.0 |
| Glucose | 30.0 to 80.0 |
| Glucosamine | trace to 3.0 |

As is seen in Table 3, the saccharide moiety of the present substance contains eight kinds of monosaccharides, and although glucose predominates, xylose and mannose are present in a relatively large amount respectively. Namely, the saccharide moiety of the present substance is a heteroglycane characterized in that the sum of the amounts of glucose, mannose and xylose occupies more than 85% by weight of the total monosaccharides.

(9) Presence of nucleic acid as a component:

Content of 0.01 to 0.50% by weight of uracil as a base of nucleic acid.

After converting phosphorus contained in the present substance into orthophosphoric acid by wet-ashing method, the orthophosphoric acid was determined by Fiske-Subbarow's method. The presence of uracil as a base of nucleic acid was confirmed by subjecting the hydrolyzate of the present substance with hydrochloric acid to high speed liquid chromatography using ultraviolet light at 254 nm. The presence of nucleic acid in the present substance was confirmed by ultraviolet absorption spectroscopy of the present substance to find out the peaks at 260 nm and 280 nm with the ratio of extiction coefficients of 0.75 to 0.95.

In addition, following the Schmidt-Thannhauser-Schneider's method ordinarily used for fractionation of nucleic acids, the fractionation of nucleic acid contained in the present substance was put to trial, however, since no nucleic acid could be fractioned, it is presumed that nucleic acid in the present substance is present in a bonded state.

(10) Infrared absorption spectrum; refer to FIGS. 2 to 19.

The infrared absorption spectra of the respective specimens obtained in Examples 1 to 18 according to the present invention are as shown in FIGS. 2 to 19. In these spectra, the broad absorption peak at 3600 to 3200 $cm^{-1}$ is considered to be OH groups which are in hydrogen bonding to various degrees because of the disappearance or the reduction of its intensity after O-methylation of the OH groups in the saccharide moiety of the present substance. The absorption peak at 1530 $cm^{-1}$ is attributable to the deformation vibration of —NH group in the protein moiety of the present substance, and the broad absorption peak at 1200 to 1000 $cm^{-1}$ is considered to be due to the asymmetrical stretching vibration of C-O-C bonding in the tetrahydropyrane ring of saccharide moiety of the present substance.

(11) Appearance and solubility to solvents:

The present substance is a powdery material pale brown to brown in colour without any taste and odor, and is soluble in water but insoluble in methanol, pyridine, chloroform, benzene and hexane.

Physiological activities of the present substance are explained as follows:

(1) Acute toxicity: Acute toxicity to mouse and rat

The acute toxicity of the present substance to ICR-JCL mice of 4 to 5 week-old with individual body weight of 21 to 24 g, and to Donryu rats of 4 to 5 week-old with individual body weight of 100 to 150 g was examined while administering intravenously, subcutaneouly, intraperitoneally or orally, observing their general symptoms, mortality and body weight during 7 days after administration and killing and autopsying. The results shown in Table 4 indicate that neither rat nor mouse showed any death even after administering the largest administable amount of the present substance, the fact making the calculation of $LD_{50}$ impossible.

TABLE 4

| | Acute toxicity to mouse and rat | | |
|---|---|---|---|
| | Route of | $LD_{50}$ (mg/kg body weight) | |
| Animal | administration | Female | Male |
| Mouse | i.v.[1] | >1300 | >1300 |
| | s.c.[2] | >5000 | >5000 |
| | i.p.[3] | >5000 | >5000 |
| | p.o.[4] | >20000 | >20000 |
| Rat | i.v. | >600 | >600 |
| | s.c. | >5000 | >5000 |
| | i.p. | >5000 | >5000 |
| | p.o. | >20000 | >20000 |

Notes:
[1]i.v.: intravonously
[2]s.c.: subcutaneously
[3]i.p.: intraperitoneally
[4]p.o.: per os (orally).

(2) Lectin-like activity

The substances showing so-called "lectin activity" have been found frequently in plant seeds, and "lectin activity" of a substance derived from a basidiomycetous fungus is disclosed in German Democratic Republic's Pat. No. 126,818. However, this patent does not refer at all to the "lectin activity" of a substance derived from a basidiomycetous fungus belonging to the genus Coriolus. The substance showing "lectin activity" found in plant seed, for example, concanavalin A obtainable from the seeds of Canavalia ensiformis and peanut lectin found in the seeds of Arachis hypogaea differs from the present substance in the composition of amino acids in the protein moiety, and the weight ratio of the protein moiety to the saccharide moiety.

In consideration of the recent recognition of the importance of "lectin activity" in physiologically active agents, particularly in antitumour agents (anti-cancer drugs), it can be said significant that the present substance show the following "lectin-like activities":

The following is the results of the examination of the specific features of the "lectin-like activities" of the present substance, especially those considered to be important from the view point of utilization as a physiologically active agent:

(i) Test on the agglutinating activity to sarcoma-180 cells

From the results of the test comprising the following procedures it has been confirmed that the present substance agglutinize sarcoma-180 cells.

Test method

Cells of sarcoma-180 were intraperitoneally transplanted to an ICR-JCL mouse at $1\times10^6$ cells/animal, and on the 7th day after transplantation, the ascites was collected from the mouse.

After adding 2 to 5 times by volume of Hanks' solution to the ascites, the mixture was centrifuged for 2 min at 300 G and the supernatant solution was discarded. After collecting the precipitate and adding Hanks' solution to the precipitate, the mixture was centrifuged again for 2 min at 300 G and the supernatant solution was discarded. The precipitate was collected, and Hanks' solution was added to the precipitate for adjusting the number of proliferated cells of Sarcoma-180 in the thus obtained solution to be $1\times10^6$/ml.

After placing 0.5 ml of the thus adjusted solution containing the suspended cells therein and 0.5 ml of an aqueous physiological saline solution in which 3 mg of the present substance was dissolved in a culture bottle and well mixing the solutions, the mixture was left for one hour at 37° C. Then, the supernatant solution was discarded, and the precipitate consisting mainly of Sarcoma-180 cells was once washed with Hanks' solution. A part of the thus washed cells was examined under a microscope to enumerate the number of agglutinated cells of Sarcoma-180.

As a control, the same procedures were repeated while using 0.5 ml of the aqueous physiological solution not containing the present substance.

Test result

Significant difference was recognized between the number of agglutinated lumps due to the present substance of 120 and the number of those due to control of 20.

(ii) Test on the inhibition by monosaccharide of agglutination of sarcoma-180 cells due to the present substance The same specimen of sarcoma-180 cells suspending in 0.5 ml of Hanks' solution at a rate of $1\times10^6$ cells/ml as in Test (i) and each 0.5 ml of the physiological saline solution containing 3 mg of the present substance and 1.5 mg of the respective monosaccharides set forth below, which was incubated for 30 min. at 37° C., then discarding the supernatant medium and washing the residue with Hanks' solution, the remaining residue was examined under a microscope to count the number of agglutinated lumps of the cells.

Test results

As is seen in the following results, of the tested monosaccharides, L-fucose L-rhamnose and methyl α-mannoside inhibited the agglutination of sarcoma-180 cells due to the present substance. Test result on the inhibitory function of monosaccharide to the agglutination of cells of Sarcoma-180 by the present substance

|  | Number of agglutinated lumps | Inhibitory activity to agglutination |
|---|---|---|
| The present substance with the monosaccharide |  |  |
| L-fucose | 27 | + |
| D-galactose | 118 | − |
| methyl α-glucoside | 115 | − |
| methyl α-mannoside | 35 | + |
| N—acetylglucosamine | 85 | ± |
| L-rhamnose | 25 | + |
| The present substance only | 124 |  |
| Blank test | 18 |  |

(iii) Test on the inhibition of erythrocyte-agglutination

In a U-type microplate with 96 wells, 25 microliters of a diluted anti-human A-type erythrocyte serum or anti-human B-type erhythrocyte serum by aqueous physiological saline solution to 16 times in volume and 25 microliters of a solution of the present substance in aqueous physiological saline solution were placed, and after reacting the mixture for 30 min. at room temperature, 25 microliters of a 4% suspension of human A-type erythrocytes or of human B-type erythrocytes in aqueous physiological saline solution was added to the reaction mixture to react them for 3 hours at room temperatures. Then, the microplate was examined under a microscope to observe the state of erythrocyte-agglutination.

As a result, the minimum concentration for inhibition of blood type-specific erythrocyte agglutination by the present substance was found to be 0.48 mg/ml.

(iv) Test on blast transformation (a) Blast transformation of human lymphocytes

Lymphocytes collected from peripheral blood of a healthy human adult were cultured for 5 days by the method of lymphocyte culture and the uptake of $^3$H-thymidine by the lymphocytes during the last 24 hours of the culture was measured. Blast transformation was determined from the extent of uptake of $^3$H-thymidine following the under-mentioned procedures.

Namely, venous blood taken from a healty adult was added slowly on Ficoll-Conray's liquid so as to divided into two layers by specific gravity, and the two layers were subjected to centrifugation for 30 min. at 400 G to obtain the lymphocytes, which were suspended in RPMI-1640 culture medium added with 20% fresh human AB-type serum at a concentration of $7.5\times10^5$ cells/ml. Into each well of microplate (Model Microtest II, made by Falcon Company), 0.2 ml of the thus prepared suspension of lymphocyte was poured, and to each well, aqueous physiological saline solution containing the present substance was poured to make the final concentration of the present substance in the solution in each well to be 0.1 mg/ml. After keeping the microplate in an incubator at 37° C. for 4 days under an atmospheric mixture (95% air and 5% carbon dioxide), 0.05 micro-Ci of $^3$H-thymidine was added into each well of the microplate and the microplate was kept for additional 24 hours in an incubator under the same conditions as above. The thus treated lymphocyte was harvested on glass fiber while using a cell harvester (Model MASH II, made by Labo Science Company). After drying the glass fiber well, it was taken into a counting vial, and after adding 3 ml of Liquid Scintillation Cocktail (PCS, made by Amersham Company) into each well, the radioactivity uptaken into the lymphocyte was determined by the scintillation counter using the unit of counts per min (c.p.m.).

Test results

The results of the test showed that the activity of causing blast transformation of the present substance corresponded to 8.000 to 10,000 c.p.m. of uptake of $^3$H-thymidine by the addition of 0.1 mg of the present substance/ml as compared to 100 to 2,000 c.p.m. of uptake of $^3$H-thymidine by control (physiological saline solution not containing the present substance). Namely, the activity of the present substance is significant over control at the level of $P<0.01$.

(b) Blast transformation of guinea-pig lymphocyte

Splenic lymphocytes of guinea pig ($1\times10^6$ cells/ml) and the present substance (50 micrograms/ml) were kept for 4 days at 37° C. under atmospheric mixture (95% air and 5% carbon dioxide), and after adding 0.5 micro-Ci of $^3$H-thymidine, the mixture was kept for additional 24 hours under the same conditions as above. By determining the uptake of $^3$H-thymidine as in (a), the stimulation index (S.I.) of the present substance was calculated from the following formula:

$$\text{Stimulation index } (S.I.) = \frac{\text{c.p.m. of the test group}}{\text{c.p.m. of control group}^{(1)}}$$

wherein mark 1) did not contain the present substance.

As a result, it was found that the stimulation index of the present substance was significantly larger than 1, the fact indicating that the present substance has activity of causing blast transformation.

The phenomenon of blast transformation shown above due to the present substance is a necessarily occurring phenomenon when lymphocytes are stimulated by an antigen to differentiate into the functional cells such as antibody-producing cells, etc. In addition, as a result of blast transformation, i.e., a result of activation of cell division, the increase of number of cells of the cell group which has a reactivity to the antigen is brought about (clonal expansion). A part of the increased cells are restored to the cells in the original state of resting, and these resting cells become the main body of "immunological effect" in the case where they are re-subjected to the stimulation of the same antibody as contrasted to the case of first stimulation. In this manner, the phenomenon of blast transformation is the phenomenon having a very important meaning in the immunoresponse. Namely, the activity of causing blast transformation of the present substance is non-specific, that is, not only a specified cell group but also cell groups in broader range are stimulated by the present substance. It is considered that such an activity brings about the non-specific immunoactivating effect and contributes to the strengthening of host resistance against the microbial infection and cancers. Actually, it has been known that activity of causing blast transformation is observed in immunotherapeutics such as BCG, OK-432, etc. against cancers, which act via non-specific immunoactivation function. As a result of examining antitumour activity of orally administered phytohemagglutinin, concanavalin A, which has been known as a representative lectin, against Sarcoma-180, 30 to 50% of antitumour activity was confirmed. This finding suggests the connection of activity of causing blast transformation to the antitumour activity.

(v) Affinity of the present substance to the surface of lymphocyte

The specific activity of the present substance to bind with the lymphocyte has been confirmed by the following experimental result while using Fluorescence Activated Cell Sorter II (FACS II, made by Beston-Dickinson Company, USA).

A thymus of C57BL/6 mouse was well untied in a phosphate buffer to obtain a single-cell suspension which was then treated with Tris-hydrochloric acid buffer containing 0.83% by weight of dissolved ammonium chloride to remove erythrocytes from the suspension and obtain an aqueous suspension of thymocytes. On the other hand, into 0.4 ml of a 5% by weight solution of the present substance in the phosphate buffer of pH of 7.0, 0.6 mg of fluorescein isothiocyanate (FITC) was added, and after stirring the mixture overnight at 4° C., the mixture was subjected to gel filtration using a column of dextran gel to remove the un-bonded FITC to the present substance and to obtain an aqueous solution of the present substance (in the phosphate buffer) labelled with FITC.

After adding $1\times10^7$ cells of a C57BL/6 mouse thymocyte into 0.1 ml of phosphate buffer solution containing the present substance labelled with FITC for 20 min. at 4° C. to react therewith, the reacted lymphocytes were analyzed by FACS (loc. cit.)

As a result, according to the observed strong fluorescence of the lymphocytes after the reaction with the present substance labelled with FITC, it was confirmed that the present substance binds to lymphocyte.

Further, it has been also confirmed that an immunosuppressive factor obtained from the ascites of an ICR-JCL mouse bearing Ehrlich carcinoma according to the method of Motoki et al. (Gann, Vol. 66(5), 569–572, 1975) binds to the lymphocyte.

However, in the case where the present substance not labelled with FITC was reacted with the lymphocytes at 4° C. for 20 min. and the reaction mixture was further reacted with the FITC-labelled immunosuppresive factor mentioned above, the strength of fluorescence of the thus reacted lymphocytes was weaker than that of lymphocyte to which the present substance had not been reacted. From these results, it is considered that the present substance inhibits the binding of the immunosuppressive factor to lymphocyte.

The fact that the present substance binds to lymphocyte has been confirmed also by the examination under an electron microscope as follows:

After reacting 25 mg of the present substance with 25 mg of ferritin, the reaction product was reacted with thymocytes of a C57BL/6 mouse in vitro.

In the case where only ferritin was reacted with thymocytes, ferritin did not bind to the surface of the thymocytes however, in the case where the present substance had been reacted with ferritin, the state of binding of the present substance to the surface of the thymocytes could be observed under a scanning electron microscope.

Such binding of the present substance to the thymocytes is considered to correspond to the antitumour effect and immunoresponse of the present substance as described in the following:

In the case where an antitumour substance stimulates lymphocytes to cause blast transformation, the binding of the substance to lymphocytes is considered to be the first step of blast transformation, however, not only a mechanism by which the antitumour effect of the substance is exhibited via the activation of lymphocytes but also another mechanism is considered, wherein the substance suppresses the binding of a principle which inhibits the activation of lymphocytes.

Namely, as shown above, the presence of an immunosuppressive factor in the ascites of cancer-bearing individual, for example, an ICR-JCL mouse bearing Ehrlich cancer has been known, and it has been found by the present inventors that the present substance inhibits the binding of this immunosuppressive factor to lymphocytes thus leading to the release of the suppression of the function of lymphocyte by the immunosuppressive factor.

Thus it is considered that the present substance, on one side, directly activates the lymphocyte, and on the other side, inhibits the binding of the immunosuppressive factor to the lymphocyte to exhibit the antitumour effect and anti-infection effect.

(vi) On the chemotaxis of macrophage to the present substance

Figure 20:
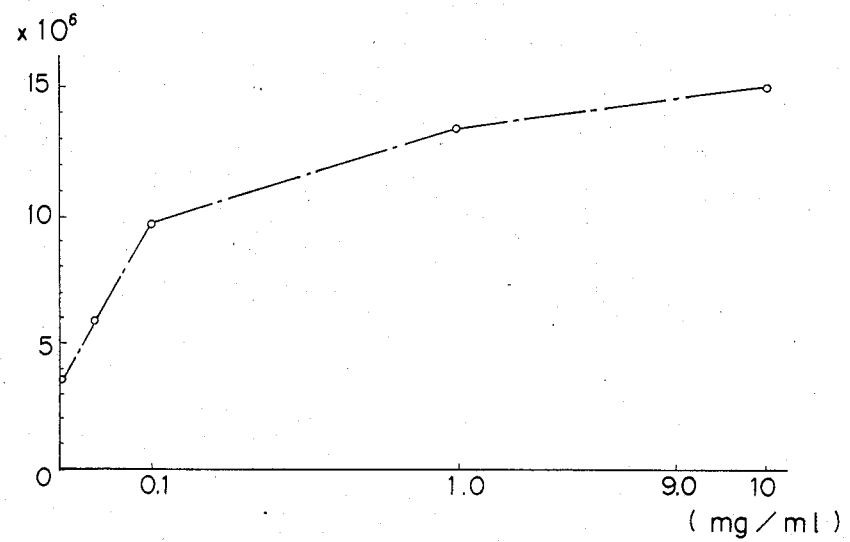

To each group of C57BL/6-female mice, 1 ml/animal of each of aqueous physiological saline solutions containing 0.03, 0.1, 1.0 or 10 mg of the present substance per ml, respectively, was intraperitoneally administered, one control group being only administered with 1 ml of the aqueous physiological saline solution. After 48 hours of the administration, all mice were subjected to venesection under ether anesthesia and 4 ml of heparin-added Hanks' solution was intraperitoneally injected to each mouse. After massaging the abdominal cavity of the mouse well, the injected solution was collected with a Komagome pipette, and the exuded cells of macrophage into the collected solution was counted by a hemocytemeter. The result of counting is shown in FIG. 20 wherein the number of exuded cells of macrophage is plotted as ordinate and the concentration of the present substance is plotted as abscissa As is seen in FIG. 20, the cells of macrophage showed a raising tendency with the raise of the concentration of the present substance. This phenomenon can be expressed that the present substance showed a remarkable activity to the chemotaxis of macrophage.

It has been known that macrophage contributes to the host resistance to cancer and infection due to the macrophage's own phagocytosis and antibody-dependent cytotoxic function, and that macrophage is deeply connected to the so-called immuno-system with a result of antigen-presentation and adjustment of immunoreaction. Moreover, in the macrophage stimulated by the present substance the function of the macrophage has been raised as mentioned above. Since the raised chemotaxis is an index of activation of macrophage, it is presumed that the present substance also reinforces the host resistance due to macrophage via activation of macrophage.

(3) Antitumour activity of the present substance (i) Activity for inhibiting the growth of solid-type Sarcoma-180 tumour Cells of Sarcoma-180 proliferated by the ordinary method were transplanted to the abdominal cavity of 4 groups of ICR-JCL mice at $1 \times 10^6$ cells/animal, and after 24 hours of transplantation, to each of 3 groups of the mice, each of the present substances was intraperitoneally administered once every other day for total 10 times at the respective dosages of 1, 10 and 100 mg/kg per time. After 25 days of the transplantation, the tumours appearing in all the mice were extirpated, and the average weight of tumours of each administered group (T) were compared with the average weight of tumours of the fourth group of mice not administered with the present substance (C) according to the following formula, and the results were expressed by the tumour-inhibiting extent:

$$\text{Tumour-inhibiting extent (\%)} = \left(1 - \frac{T}{C}\right) \times 100.$$

Furthermore, in another test, the present substance was orally administered, in stead of intraperitoneal injection, to the two groups of tumour-transplanted mice at the respective dosages of 50, 100 and 250 mg/kg/time, respectively, and the tumour-inhibition was examined in the same manner as above.

(ii) Activity for inhibiting the growth of Erhlich Ascites Tumour

After incubating $1 \times 10^6$ cells of Ehrlich ascites tumour (hereinafter refer to as EC cells) in Hanks' solution containing 5 mg of each of the present substances for 3 hours at 37° C., the thus incubated cells were transplanted into the abdominal cavity of ICR-JCL mouse (10 animals per group) at $1 \times 10^6$ cells/animal. The mortality of the treated mice was observed for 20 days after transplantation to find the survival rate of the mice and the antitumour activity of the present substance administered at 50 mg/kg/time as mentioned in (i), the body weight of the mouse being 20 g in average. All the mice of control group to which tumour cells were transplanted but the present substance was not administered died during 20 days after transplantation due to the tumour.

The results of the tests (i) and (ii), as will be shown in Table 5, verify the excellent activity for inhibiting the growth of the Ehrilich Acites tumor of the present substance.

(iii) Activity for inhibiting the growth of Lewis lung carcinoma

A cubic fragment of 3 mm side of tubercle of Lewis lung carcinoma was transplanted subcutaneously into the back on each of 2 groups of female C57BL/6 mouse of 6-week-old.

After 24 hours of transplantation, to each of one group of the mice, the present substance was intraperitoneally administered once every other day for total 10 times at the dosage of 10 mg/kg per time. After 25 days of the transplantation, the tumours appearing in all the mice were extirpated, and the average weight of tumours of each administered group (T) were compared with the average weight of tumours of the other group of mice not administered with the present substance (C) according to the following formula, and the results were expressed by the tumour-inhibiting extent:

$$\text{Tumour-inhibiting extent (\%)} = \left(1 - \frac{T}{C}\right) \times 100.$$

Furthermore, in another test, the present substance was orally administered, in stead of intraperitoneal injection, to each of the tumour-transplanted mice at the dosage of 250 mg/kg/time and the tumour-inhibition was examined in the same manner as above.

The results of the test are shown below.

|  | Inhibition extent (%) |
| --- | --- |
| intraperitoneal administration | 59.7 |
| oral administration | 69.3 |

(iv) Activity for inhibiting the growth of B-16 melanoma

A cubic fragment of 3 mm side of tubercle of B-16 melanoma was transplanted subcutaneously into the back on each of 2 groups of female C57BL/6 mouse of 6-week-old.

After 24 hours of the transplantation, the present substance was intraperitoneally administered as a solution in aqueous physiological saline solution at the daily dosage of 10 mg/kg to each mouse of the one group once a day for 10 days running Thereafter, the life-prolongation rate of the present substance was evaluated. In addition, to the other group (the control group), only the aqueous physiological saline solution was administered in the same manner as in the other group.

The life-prolongation rate was obtained from the following formula:

$$\text{Life-prolongation rate (\%)} = \frac{T_1 - C_1}{C_1} \times 100$$

wherein $T_1$ is the average survival days of the test group and $C_1$ is the average survival days of the control group.

Furthermore, in another test, the present substance was orally administered, instead of intraperitoneal injection, to each mouse of test group at the daily dosage of 250 mg/kg and the life-prolongation rate was obtained in the same manner as above.

The results of the test are shown below.

|  | life-prolongation rate |
| --- | --- |
| intraperitoneal administration | 136.0% |
| oral administration | 135.1% |

Since the present substance shows an excellent activity for inhibiting the growth of malignant tumor cells, it is useful as an inhibiting agent, particularly an orally administerable inhibiting agent. In addition, since the present substance has lectin-like physiological activities, it has an immunomodulating activity to the host, and not only for cancer-bearing patients but also for all patients it exhibits a prominent effectiveness in activating the immunity and preventing infectious diseases due to viruses and bacteria.

As the malignant tumor in which the growth of the tumor is inhibited by the present substance, stomach cancer, lung cancer, colon cancer, rectal cancer, breast cancer, esophageal cancer, hepatoma, cancer of kidney, bladder cancer, uterime cancer, ovarian cancer, cancer of the pancreas, cancer at region of head and neck, embryonal carcinoma, cerebral tumor, leukemia and malignant lymphoma may be mentioned.

The present compound can be used in a dosage unit form such as a drug or a pharmaceutical composition. The composition may contain 0.01 to 99.5% by weight, preferably 0.1 to 90% by weight, of the present compound as an active ingredient.

The pharmaceutical composition may contain a pharmaceutically acceptable carrier, diluent or adjuvant as well as at least one of the present substance. Further, the composition may contain filler, extender, binder, wetting agent, disintegrant, retarder of dissolution, accelerator of reabsorption, adhesive carrier and/or lubricant, for example, starch, mannitol, silicic acid, cellulose derivative, gelatin, alginate, glycerol, agar, calcium carbonate, sodium hydrogen carbonate, paraffin, quartarnary ammonium compound, glycerol monostearate, kaolin, bentonite, talc, potassium stearate, polyethylene glycol and the like.

Although the pharmaceutical composition is ordinarily administered orally to patients, according to the conditions of the patient, it can be intraperitoneally administered in the form of injection. The dosage form for oral administration may be tablet, capsule, powder, granule, pill, ampoule or the like. The composition may be in the form of pharmaceutically acceptable emulsion, solution, suspension and the like.

The oral dosage of the present substance is ordinarily 1 to 100 mg/kg body weight/day preferably 5 to 90 mg/kg body weight/day, that is, it exhibits an excellent tumour-imhibiting effect at a very small amount of administration as compared to the hetherto reported glycoprotein substance or polysaccharide derived from a basidiomycetous fungus.

The present invention will be more precisely explained while referring to Examples as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE 1

Preparation of the present compound

A strain CM-101 of Coriolus versicolor (Fr.) Quél. [FERM-P 2412, (ATCC 20547)] was cultured in a culture medium comprising of 5% by weight of glucose, 0.2% by weight of peptone, 0.3% by weight of yeast extract, 0.1% by weight of $KH_2PO_4$ and 0.1% by weight of $MgSO_4.7H_2O$ for ten days, and the mycelia which proliferated on the surface of the culture medium was homogenized with an aqueous physiological solution to be a seed culture for breeding. The seed culture was inoculated in each 200 ml of the same culture medium as above in 100 culture bottles of 1 liter in capacity, and cultured for 25 days at 25° to 27° C. to obtain the propagated mycelia in a yield of 2.0 to 4.5 g per culture bottle.

One hundred grams of the thus obtained mycelia was extracted with 3 liters of aqueous 0.1N sodium hydroxide solution at 97° C. for one hour, and after removing the extract residue, the thus obtained extract was neutralized with acid and condensed.

Subsequently, after desalting the condensate was treated by dialysis and ultra-filtration to remove the low-molecular weight substances of molecular weight of below 5,000. The thus treated condensate from which the low-molecular weight substances have been removed (or the powdery substance obtained by drying the thus treated condensate) was mixed with a phosphate buffer to maintain the pH of the mixture at 3.5, and after neutralizing the supernatant solution obtained by centrifugation of the mixture, the neutralized supernatant was subjected to ultrafiltration under 1.5 kg/cm$^2$ and at a temperature of 10° C. while stirring, cooling and utilizing an ultrafiltration apparatus (Model: Tablemount Highflow-2000, made by Amicon Company, with the diaphragm of grade DM-5) to remove the salts in the supernatant. After condensing the desalted supernatant, a phosphate buffer was added to the condensate to maintain the pH of the resultant mixture at 3 and the mixture was centrifuged to collect the precipitate.

The above-mentioned series of procedures, by which the fractions precipitating at the pH of 3.5 under the condition of the ion strength 0.30$\mu$ at a temperature of 5° C. for 2 hours were discarded and then only the fractions precipitating from the remaining solution after maintaining the pH at 3.0 thereof under the same condition were collected, comprises a method of fractionation by precipitation at an isoelectric point within a range of pH 3.0 to 3.5.

The thus obtained precipitate was re-dissolved in water while adjusting the pH of the thus obtained solution to 7, and was desalted by the same method of desalting as above to purify the solution, and then dried to be the present substance in a powdery state.

Molecular weight; elementary analytical data; colour reactions of sugars and proteins; specific rotatory power, infrared absorption spectrum; results of amino acid analysis, analytical data on amino acids, respectively on N-end and C-end, sugar components of the saccharide moiety, respective contents of protein- and sugar moiety; ultra-violet absorption spectrum; respective contents of uracil and phosphorus contained in organophosphorus compound, both of which showing the presence of nucleic acid and specific physiological properties of the present substance, determined by the present inventors, were shown in Table 5. In Table 5, "t" means "trace". The methods for determining the above-concretely-mentioned properties of the present substance were as follows:

Molecular weight

After preparing a 0.3% by weight solution of the present substance by dissolving it into an aqueous 0.1M potassium chloride solution, the sedimantation velocity of the present substance was determined at 25° C. for 5 hours at a liquid column height of 1.7 mm in ultra high speed centrifuge at 22,000 r.p.m., and the molecular weight of the present substance was obtained by the usual calculation following the ultra-high centrifugal method for obtaining molecular weight.

Specific rotatory power

The optical rotation of an aqueous 0.1% by weight solution of the present substance for D line of sodium (589 nm) was determined in a cell of 5 cm in length, and the value was calculated to obtain the specific rotatory power of the present substance.

Amino acid analysis

In a glass tube, 10 mg of the present substance was placed as the specimen and, after adding 4 ml of 6 N hydrochloric acid solution and freezing the content with dry-ice and acetone mixture, the tube was sealed under a reduced pressure and then heated for 24 hours at 110° C. for hydrolyzing the substance. After collecting and drying the reaction product, the dried matter was dissolved into 30 to 40 ml of a citrate buffer of pH 2.2, and the solution was subjected to an apparatus for amino acid analysis to obtain the data.

Analytical data on N-terminal amino acid

While using 7 mg of the present substance as the specimen, analytical data on N-terminal amino acid of the present substance was determined by DNP method with trimethylamine as follows:

After dissolving 7 mg of the specimen into 0.7 ml of water, 0.14 ml of aqueous 5% by weight solution of trimethylamine and 0.7 ml of ethanolic 5% by weight solution of 1-fluoro-2,4-dinitrobenzene were added to the solution, and the mixture was stirred for 3 hours at 28° C. in the shade. After adding a few drops of water and a small amount of an aqueous solution of trimethylamine to the mixture and washing the mixture 4 times with diethyl ether, a few drops of concentrated hydrochloric acid were added to the aqueous layer, and after further washing the aqueous acidic layer with ether three times, the pH of the aqueous layer was adjusted to the pH of 6N hydrochloric acid and heated for 20 hours at 110° C. to effect hydrolysis. After adding water to the thus obtained hydrolyzate to adjust the pH of the hydrolyzate to the pH of about 1N hydrochloric acid, the mixture was extracted three times with diethyl ether. The etheric layer was dried and then used as the specimen for analysis by high-speed liquid chromatography (with a column of Zorbax ® O.D.S. of 4.6 mm in diameter and of 250 mm in length) while eluting with a gradient eluting system of acetonitrile- sodium dihydrogen phosphate and using an ultraviolet of 254 nm for detection.

Analysis of C-terminal amino acid

Into a solution obtained by dissolving 250 mg of the present substance as a specimen in 9.46 ml of 0.0025M Trisbuffer of pH 8.6, 0.54 ml of an aqueous solution of 0.3 unit of carboxypeptidase-DFP (made by SIGMA Company) was added to make the total volume of the mixture 10 ml. While keeping the temperature of the thus obtained mixture at 30° C., each 1 ml of the specimen was fractionally collected every predetermined interval, and 1.5 ml of aqueous 50% by weight solution of acetic acid was added to each specimen to pH of 2 for stopping the enzymatic reaction, and the thus sedimented precipitate was collected, dried and dissolved into a buffer of pH 2.2, and then subjected to an automatic amino acid analyzer to determine the free amino acid.

Analysis of sugar components of saccharide moiety

In a glass ampoule, 10 mg of the present substance was placed as a specimen, and after adding 1.0 ml of aqueous 1N sulfuric acid solution in the ampoule, the mixture was heated at 100° C. for 16 hours to effect hydrolysis, and after neutralizing the hydrolyzate at room temperature with barium carbonate and removing the thus sedimented precipitate by filtration, the filtrate was reduced by the addition of sodium boron hydride and the reactant was desalted with an ion-exchanging resin. After condensing the desalted solution to dryness and removing the remaining boron compound under a reduced pressure with methanol by azeotropic distillation, the residue was dried to solid. The residual solid was dissolved in pyridine and then acetylated with acetic anhydride at 100° C. After removing the reagent under a reduced pressure remaining in the reaction mixture containing acetylated products, the residue was dissolved in carbon tetrachloride and subjected to gas-chromatography.

Determination of uracil as a base of nucleic acid

After hydrolyzing the present substance with hydrochloric acid, the hydrolyzate was subjected to high-speed liquid chromatography with Solvacks® CN column while using aqueous 6% by weight solution of acetic acid as the moving phase and examining the eluent with ultra-violet light of 254 nm to detect the presence of uracil.

Quantitative determination of phosphorus contained in organophosphorus compound for confirming the presence of nucleic acid in the present substance After decomposing organophosphorus components of the present substance into orthophosphoric acid by the wet-ashing method, the resultant phosphoric acid was quantitatively determined. Namely, 2 ml of an aqueous solution containing 20 mg of the present substance and 2 ml of aqueous 5N sulfuric acid solution were heated in a Kjeldahl decomposition flask until the content turned to brown in colour, and then after cooling, one to two drops of aqueous 30% by weight solution of hydrogen peroxide were added to the content of the flask, and the flask was again heated until the content became colouless. After cooling the flask, one ml of pure water was added to the content of the flask, and after heating the flask for 5 min. in a hot-water bath and adjusting the volume of the content to a predetermined value, a part of the content was subjected to Fiske-Subbrow's method for obtaining the amount of orthophosphoric acid in the decomposed specimen of the present substance.

EXAMPLES 2 TO 18

In stead of the strain CM-101 of *Coriolus versicolor* (Fr.) Quél. (FERM-P 2412, ATCC 20547), each of the respective strains of the fungi shown in Table 1 was used as the starting material for obtaining the present substance by the same procedures as in Example 1 except for carrying out the fractionation by precipitation at an isoelectric point in the range respectively shown in Table 5 different from pH 3.0 to 3.5. The properties of the thus obtained substances of the present invention in Examples 2 to 18 determined by the same respective methods are also shown in Table 5 and thereafter. In Table 5, "t" means "trace".

TABLE 5

Physical and physiological properties of the present substance

| Item | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| Number of deposition FERM-P: | | 2412 | 2413 | 2414 | 2415 | 2416 | 2417 | 2418 | 2419 | 2420 | 2421 | 2422 | 2423 | 2424 | 2425 | 2426 | 2711 | 2712 | 988 |
| Range of pH in precipitation at isoelectric point | | 3.0–3.5 | 3.5–4.0 | 4.0–4.5 | 3.0–4.0 | 3.0–4.5 | 2.5–3.0 | 2.5–3.5 | 2.5–4.0 | 2.5–4.5 | 2.5–5.0 | 4.5–5.0 | 3.5–5.0 | 2.5–4.5 | 3.0–5.0 | 2.5–4.5 | 2.5–5.0 | 2.5–5.0 | 2.5–4.5 |
| Molecular weight range ($\times 10^4$) | | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 | 0.5–30 |
| Elementary analytical data (%) | | | | | | | | | | | | | | | | | | | |
| C: | | 46.0 | 47.2 | 40.5 | 44.3 | 48.5 | 39.8 | 44.1 | 42.6 | 38.5 | 40.9 | 41.8 | 37.6 | 43.3 | 42.6 | 40.1 | 45.4 | 42.7 | 38.3 |
| H: | | 6.2 | 7.8 | 5.3 | 6.9 | 5.5 | 6.3 | 7.0 | 6.2 | 6.2 | 5.8 | 6.4 | 7.2 | 5.8 | 7.0 | 7.5 | 5.0 | 5.8 | 6.5 |
| N: | | 10.2 | 6.0 | 6.9 | 7.5 | 10.3 | 12.1 | 7.0 | 8.8 | 7.0 | 5.5 | 4.5 | 6.8 | 7.3 | 9.2 | 9.9 | 11.6 | 10.1 | 7.6 |
| S: | | t | 0.6 | 0.3 | 2.3 | t | 0.5 | 1.5 | 1.8 | 0.8 | t | 1.2 | 1.3 | 0.9 | 0.5 | 1.8 | 2.0 | t | 0.8 |
| P: | | 0.7 | 0.8 | 0.5 | 0.6 | 0.3 | 1.0 | 0.2 | t | t | 0.7 | 0.2 | 0.4 | 0.1 | 0.6 | t | 0.3 | 0.7 | 0.5 |
| O: | | 36.9 | 37.6 | 46.5 | 38.4 | 35.4 | 40.3 | 40.2 | 40.6 | 47.5 | 47.1 | 45.9 | 46.7 | 42.6 | 40.1 | 40.7 | 35.7 | 40.7 | 46.3 |
| | | 32.2 | 42.2 | 41.9 | 44.7 | 32.5 | 24.9 | 30.7 | 34.0 | 37.9 | 46.0 | 49.7 | 41.6 | 40.2 | 42.9 | 40.7 | 37.8 | 35.3 | 40.1 |
| Content of saccharide (% by weight) | | 67.8 | 57.8 | 58.1 | 55.3 | 67.5 | 75.1 | 69.3 | 66.0 | 62.1 | 54.0 | 50.3 | 58.4 | 59.8 | 57.1 | 59.3 | 62.2 | 64.7 | 59.9 |
| Content of protein (% by weight) | | | | | | | | | | | | | | | | | | | |
| Saccharide component and its content (% by weight) | fucose | 1.1 | 3.9 | 2.1 | 0.6 | 1.8 | 2.3 | 2.7 | 2.6 | 2.9 | 2.0 | 1.2 | 2.8 | 2.0 | 2.7 | 1.8 | 3.6 | 2.9 | 1.5 |
| | ribose | 1.0 | t | t | 1.8 | 1.5 | 0.8 | t | 0.9 | 1.6 | 1.1 | t | t | 1.3 | 1.0 | 1.2 | t | 1.0 | 1.3 |
| | arabinose | 5.3 | 1.9 | 2.3 | 0.3 | 0.5 | 2.6 | 0.9 | 4.7 | 1.5 | 0.8 | 0.5 | 1.9 | 3.4 | 0.6 | 0.4 | 1.8 | 1.6 | 1.9 |
| | xylose(1) | 13.5 | 34.9 | 19.5 | 23.8 | 23.5 | 31.0 | 30.0 | 32.4 | 22.6 | 20.2 | 19.8 | 21.7 | 31.6 | 28.3 | 22.5 | 18.2 | 19.3 | 16.5 |
| | mannose (2) | 10.6 | 13.2 | 17.0 | 16.3 | 11.3 | 12.4 | 13.9 | 13.6 | 15.1 | 14.1 | 12.3 | 11.4 | 10.9 | 12.5 | 14.0 | 13.5 | 11.5 | 15.0 |
| | galactose | 2.0 | 4.1 | 6.2 | 3.5 | 3.1 | 2.9 | 2.8 | 2.0 | 2.6 | 2.4 | 5.8 | 4.1 | 3.5 | 2.8 | 2.5 | 2.6 | 2.7 | 4.0 |
| | glucose (3) | 66.5 | 42.0 | 52.9 | 53.7 | 58.3 | 48.0 | 49.7 | 43.6 | 53.7 | 59.6 | 61.4 | 58.1 | 46.3 | 52.1 | 57.6 | 61.3 | 61.0 | 60.8 |
| | glucosamine | t | t | t | t | t | t | t | 0.2 | t | t | t | t | 1.0 | t | t | t | t | t |
| | Sum of (1), (2) and (3) | 90.6 | 90.1 | 89.4 | 93.8 | 93.1 | 91.4 | 93.6 | 89.6 | 91.4 | 93.9 | 93.5 | 91.2 | 88.8 | 92.9 | 94.1 | 93.0 | 91.8 | 92.3 |
| Amino acid component content (% by weight) | aspartic* acid | 14.6 | 10.8 | 12.6 | 14.9 | 12.2 | 13.0 | 13.9 | 14.0 | 13.5 | 15.3 | 12.0 | 16.0 | 10.7 | 11.6 | 13.1 | 14.7 | 14.4 | 13.1 |
| | threonine* | 4.1 | 6.0 | 4.9 | 5.8 | 4.2 | 4.4 | 4.1 | 4.8 | 5.2 | 4.9 | 4.1 | 4.9 | 4.2 | 4.2 | 4.4 | 4.1 | 4.6 | 4.2 |
| | serine* | 5.1 | 4.1 | 5.7 | 3.0 | 4.1 | 3.5 | 3.6 | 3.2 | 3.1 | 3.4 | 3.9 | 3.6 | 3.8 | 3.3 | 3.7 | 5.0 | 3.5 | 3.8 |
| | glutamic acid* | 14.5 | 15.2 | 11.2 | 10.4 | 13.5 | 12.6 | 15.5 | 10.8 | 11.6 | 14.7 | 10.9 | 11.2 | 14.1 | 15.8 | 12.6 | 12.2 | 12.7 | 13.0 |
| | proline | 3.5 | 7.3 | 1.0 | 2.5 | 6.0 | 6.4 | 5.0 | 3.5 | 6.8 | 2.8 | 4.7 | 3.3 | 5.3 | 6.1 | 6.9 | 2.7 | t | 2.6 |
| | glycine* | 8.6 | 6.0 | 9.8 | 7.9 | 7.3 | 6.5 | 7.1 | 8.0 | 7.4 | 7.3 | 7.1 | 6.2 | 7.1 | 6.4 | 7.4 | 6.7 | 8.1 | 9.4 |
| | alanine* | 9.0 | 9.5 | 12.4 | 6.5 | 8.2 | 10.0 | 11.0 | 9.7 | 10.1 | 8.4 | 11.2 | 10.8 | 7.8 | 8.5 | 10.0 | 7.6 | 11.1 | 9.3 |
| | cystine | t | t | t | t | t | t | 0.1 | t | t | t | t | 0.1 | t | t | t | 0.1 | t | t |
| | valine* | 6.3 | 11.0 | 12.0 | 11.0 | 7.7 | 8.2 | 7.9 | 8.3 | 6.9 | 10.1 | 9.0 | 6.7 | 7.0 | 8.5 | 9.1 | 10.5 | 10.3 | 9.7 |
| | methionine | 0.9 | 1.0 | t | 3.6 | 2.6 | 2.3 | 1.6 | 2.7 | 1.9 | 2.2 | 3.1 | 2.4 | 3.3 | 1.4 | 0.8 | 1.3 | 2.9 | 1.1 |
| | cystathionine | 1.0 | 2.5 | 0.2 | t | 0.5 | 1.1 | 2.1 | 1.9 | 2.4 | 2.3 | 1.6 | 1.2 | 0.9 | 1.4 | t | 1.0 | 2.7 | 1.8 |

TABLE 5-continued

Physical and physiological properties of the present substance

| Item | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| | isoleucine* | 3.3 | 3.6 | 8.2 | 3.7 | 5.9 | 3.8 | 3.1 | 4.2 | 5.1 | 3.2 | 5.6 | 4.3 | 5.7 | 6.6 | 5.0 | 6.9 | 3.9 | 4.8 |
| | leucine* | 8.0 | 8.7 | 11.5 | 12.6 | 10.4 | 9.5 | 10.5 | 8.1 | 12.0 | 9.2 | 10.1 | 11.1 | 12.1 | 9.6 | 9.2 | 9.4 | 8.8 | 9.2 |
| | tyrosine | 0.3 | 4.3 | 0.7 | 1.8 | 3.2 | 2.6 | 1.1 | 4.2 | 0.9 | 2.6 | 3.6 | 0.3 | 3.9 | 4.1 | 3.2 | 0.2 | 0.5 | 2.9 |
| | phenylalanine* | 7.5 | 4.2 | 3.3 | 8.4 | 6.0 | 6.9 | 4.4 | 5.8 | 6.5 | 4.7 | 4.1 | 5.9 | 6.2 | 4.6 | 5.8 | 5.7 | 5.3 | 6.0 |
| | tryptophan | t | t | 0.2 | t | t | 0.1 | t | t | t | 0.1 | t | t | t | t | 0.1 | 0.2 | t | t |
| | ornithine | 0.3 | 0.4 | 1.3 | 0.5 | 1.5 | 1.0 | 1.0 | 0.3 | 0.9 | 1.3 | 1.4 | 1.1 | 0.9 | 1.0 | 1.6 | 0.8 | 1.1 | 1.4 |
| | lysine | 3.5 | 1.2 | 1.2 | 1.8 | 2.9 | 2.8 | 2.2 | 1.6 | 2.9 | 2.4 | 1.9 | 2.9 | 1.8 | 2.0 | 3.1 | 2.6 | 2.3 | 2.8 |
| | histidine | 1.7 | 1.0 | 0.7 | 0.3 | 2.0 | 1.9 | 0.5 | t | 0.9 | 1.2 | 0.4 | 1.7 | t | 1.8 | 0.7 | 1.1 | 1.8 | 0.6 |
| | arginine | 1.8 | 2.0 | 1.1 | 3.5 | 1.7 | 1.9 | 2.6 | 1.9 | 1.9 | 2.0 | 2.7 | 2.3 | 3.4 | 1.6 | 1.8 | 1.7 | 3.1 | 2.9 |
| | (ammonia) | 6.0 | 1.2 | 2.0 | 1.8 | 2.1 | 1.5 | 2.8 | 3.5 | 3.0 | 1.9 | 2.6 | 4.1 | 1.8 | 1.5 | 2.5 | 5.6 | 2.9 | 1.4 |
| | total sum of those with* | 81.0 | 79.1 | 91.6 | 84.2 | 79.5 | 78.4 | 81.1 | 76.9 | 79.4 | 81.2 | 78.0 | 80.7 | 78.7 | 79.1 | 79.3 | 82.8 | 82.7 | 82.5 |
| Presence (+) or absence (−) of amino acid at N— end | tyrosine | + | + | + | + | + | + | + | + | + | + | + | + | + | + | + | + | + | + |
| | leucine | + | + | + | + | + | + | + | + | + | + | + | + | + | + | + | + | + | + |
| | alanine | + | + | + | + | + | + | + | + | + | + | + | + | + | + | + | + | + | − |
| | others | − | − | − | − | − | − | − | − | − | − | − | − | − | − | − | − | − | − |
| Lectin-like activities | | | | | | | | | | | | | | | | | | | |
| Reactivity to monosaccharide | | | | | | | | | | | | | | | | | | | |
| | glucose | + | + | + | + | + | + | + | + | + | + | + | + | + | + | + | + | + | + |
| | mannose | + | + | + | + | + | + | + | + | + | + | + | + | + | + | + | + | + | + |
| | rhamnose | + | + | + | + | + | + | + | + | + | + | + | + | + | + | + | + | + | + |
| | galactose | − | − | − | − | − | − | − | − | − | − | − | − | − | − | − | − | − | − |
| Activity according to presence or absence of Ca++ ion | | | | | | | | | | | | | | | | | | | |
| in presence of Ca++ | | + | + | + | + | + | + | + | + | + | + | + | + | + | + | + | + | + | + |
| in absence of Ca++ | | − | − | − | − | − | − | − | − | − | − | − | − | − | − | − | − | − | − |
| Inhibition of erythrocyte-agglutination | | + | + | + | + | + | + | + | + | + | + | + | + | + | + | + | + | + | + |
| Agglutination of tumour cells | | + | + | + | + | + | + | + | + | + | + | + | + | + | + | + | + | + | + |
| Stimulation of blast transformation | | + | + | + | + | + | + | + | + | + | + | + | + | + | + | + | + | + | + |
| Affinity to the surface of lymphocytes | | + | + | + | + | + | + | + | + | + | + | + | + | + | + | + | + | + | + |
| Exudation of macrophage | | + | + | + | + | + | + | + | + | + | + | + | + | + | + | + | + | + | + |

TABLE 5-continued

Physical and physiological properties of the present substance

| Item | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| (chemotaxy) Amino acid sequence from C—end of protein moiety Presence (+) or absence (−) of leucine-phenylalanine-valine | + | + | + | + | + | + | + | + | + | + | + | + | + | + | + | + | + | + |
| Presence (+) or absence (−) of other amino acid sequence | − | − | − | − | − | − | − | − | − | − | − | − | − | − | − | − | − | − |
| Specific rotatoty Power | −1 | −2 | 0 | +1 | −1 | −8 | +5 | −4 | +2 | −3 | +5 | +2 | 0 | −1 | −2 | +1 | −1 | +3 |
| Ultraviolet absorption | | | | | | | | | | | | | | | | | | |
| E at 280 nm | 52 | 55 | 57 | 50 | 65 | 56 | 63 | 57 | 50 | 45 | 42 | 43 | 46 | 46 | 53 | 53 | 42 | 45 |
| E at 260 nm | 67 | 73 | 69 | 71 | 77 | 67 | 75 | 68 | 56 | 48 | 44 | 47 | 48 | 56 | 69 | 58 | 53 | 55 |
| E280/E260 | 0.77 | 0.76 | 0.82 | 0.70 | 0.85 | 0.83 | 0.84 | 0.84 | 0.90 | 0.93 | 0.94 | 0.91 | 0.95 | 0.82 | 0.77 | 0.91 | 0.79 | 0.81 |
| Content of uracil (% wt.) as base of nucleic acid | 0.27 | 0.45 | 0.30 | 0.40 | 0.36 | 0.24 | 0.32 | 0.31 | 0.19 | 0.16 | 0.04 | 0.15 | 0.02 | 0.21 | 0.41 | 0.19 | 0.23 | 0.22 |
| Content of organic phosphorus (% wt. as P₂O₅) | 0.09 | 0.11 | 0.07 | 0.09 | 0.10 | 0.06 | 0.07 | 0.10 | 0.05 | 0.02 | 0.01 | 0.03 | 0.04 | 0.02 | 0.12 | 0.07 | 0.04 | 0.05 |
| Inhibition extent to Sarcoma-180 on mouse by i.p.[1] administration | | | | | | | | | | | | | | | | | | |
| % at 1 mg/kg/time | 100 | 100 | 100 | 100 | 99 | 100 | 99 | 100 | 100 | 100 | 100 | 99 | 100 | 100 | 100 | 98 | 99 | 99 |
| % at 10 mg/kg/time | 100 | 100 | 100 | 100 | 100 | 100 | 100 | 99 | 100 | 100 | 100 | 100 | 100 | 99 | 100 | 99 | 98 | 99 |
| % at 100 mg/kg/time | 100 | 100 | 100 | 100 | 100 | 99 | 100 | 100 | 100 | 100 | 100 | 100 | 100 | 100 | 100 | 99 | 99 | 99 |
| % at 100 mg/kg/time by p.o.[2] administration | | | | | | | | | | | | | | | | | | |
| % at 50 mg/kg/time | 88 | 85 | 83 | 82 | 85 | 81 | 85 | 85 | 87 | 83 | 80 | 83 | 86 | 81 | 81 | 83 | 80 | 80 |
| % at 100 mg/kg/time | 90 | 86 | 86 | 83 | 86 | 84 | 85 | 87 | 88 | 85 | 82 | 84 | 88 | 82 | 81 | 84 | 82 | 82 |
| % at 250 mg/kg/time | 90 | 89 | 90 | 86 | 87 | 87 | 88 | 89 | 90 | 89 | 82 | 86 | 90 | 85 | 85 | 87 | 83 | 85 |
| Inhibition extent to Ehrlich ascites tumour on mouse by i.p. administr. | | | | | | | | | | | | | | | | | | |
| % at 50 mg/kg/time | 100 | 100 | 100 | 100 | 100 | 100 | 100 | 100 | 100 | 100 | 100 | 100 | 100 | 100 | 100 | 100 | 100 | 100 |
| Survival rate of mouse transplanted with Ehrlich ascites tumour cells for 20 days | 8/10 | 8/10 | 8/10 | 8/10 | 7/10 | 8/10 | 8/10 | 8/10 | 8/10 | 8/10 | 8/10 | 8/10 | 8/10 | 8/10 | 7/10 | 8/10 | 8/10 | 8/10 |

Notes:
[1]intraperitoneous injection.
[2]oral administration.

In addition, each of the substances obtained in Examples 1 to 18 showed the following respective colour reactions of saccharide and of protein:

| | | Colour |
|---|---|---|
| (1) | Colour reaction of saccharide: | |
| | α-naphthol - sulfuric acid reaction: | purple |
| | indole - sulfuric acid reaction | brown |
| | anthrone - sulfuric acid reaction | greenish blue |
| | phenol - sulfuric acid reaction | brown |
| | tryptophane - sulfuric acid reaction | purplish brown |
| | thioglycolic acid - sulfuric acid reaction | greenish brown |
| | orcinol - hydrochloric acid reaction | greenish brown |
| (2) | Colour reaction of protein: | |
| | Lowry-Folin reaction | blue |
| | Ninhydrin reaction on the hydrolyzate of the present substance by hydrochloric acid | purplish blue |

According to infrared absorption spectoscopy, each of the present substances showed absorption maximas in ranges of 3600 to 3200 cm$^{-1}$ and 1200 to 1000 cm$^{-1}$, and at 1600 and 1530 cm$^{-1}$.

What is claimed is:

1. A nucleic acid-containing glycoprotein, having a molecular weight of from 5,000 to 300,000 as determined by the ultracentrifugation method; the ratio of the weight of its protein moiety, as determined by Lowry-Folin's method, to the weight of its saccharide moiety, as determined by the phenosulfuric acid method, being from 50:50 to 80:20; the saccharide moiety containing fucose, ribose, arabinose, xylose, mannose, galactose, glucose and glucosamine, and the total weight of said xylose, said mannose and said glucose being more than 85% by weight of the total weight of said saccharides; the protein moiety containing aspartic acid, threonine, serine, glutamic acid, proline, glycine, alanine, cysteine, valine, methionine, cystathionine, isoleucine, leucine, tyrosine, phenylalanine, tryptophan, ornithine, lysine, histidine and arginine, and the total weight of said aspartic acid, said threonine, said serine, said glutamic acid, said glycine, said alanine, said phenylalanine, said valine, said leucine and said isoleucine being more than 75% by weight of the total weight of all of said amino acids; the amino acid at its N-end being tyrosine, leucine or alanine; the amino acid sequence at its C-end being leucine to phenylalanine to valine, the terminal amino acid being leucine; its elementary composition being from 35.2 to 49.3% of C, from 4.8 to 8.0% of H. from 4.3 to 12.3% of N, from a trace amount to 2.5% of S, from a trace amount to 1.2% of P and the balance being 0, isoelectric point being from pH 2.5 to pH 5.0; nucleic acid containing 0.01 to 0.50% by weight of uracil as a base of nucleic acid; and nucleic acid-containing glycoprotein showing infrared absorption maxima at 3600-3200 cm$^{-1}$, 1530 cm$^{-1}$ and 1200-1000 cm$^{-1}$, said nucleic acid-containing glycoprotein being obtained by extracting fruit bodies, mycelia or cultured mycelia of a basidiomycetous fungus belonging to the genus Coriolus with hot water or an aqueous 0.01 to 2.0N alkali solution at a temperature of 80° to 100° C. for 1 to 8 hours, neutralizing the obtained extract, subjecting the neutralized extract to dialysis and/or ultra-filtration thereby removing a low molecular weight substance having a molecular weight of below 5,000 and fractionally collecting the fractions precipitating under the conditions of the pH of 2.5 to 5.0, of the ion strength of 0.1 to 3.1μ at a temperature of 5° to 25° C.

2. A nucleic acid-containing glycoprotein according to claim 1, wherein said basidiomycetous fungus is selected from the group consisting of *Coriolus versicolor* (Fr.) Quél. *Coriolus hirsutus* (Fr.) Quél., *Coriolus pergamenus* (Fr.) Pat., *Coriolus consors* (Berk.) Imaz., *Coriolus pubescens* (Fr.) Quél., *Coriolus biformis* (Klotz.) Pat. and *Coriolus conchifer* (Schw.) Pat.

3. A nucleic acid-containing glycoprotein according to claim 2, wherein said basidiomycetous fungus is *Coriolus versicolor* (Fr.) Quél.

4. A nucleic acid-containing glycoprotein according to claim 1, wherein the protein moiety thereof consists of 10 to 20% by weight of aspartic acid, 4 to 6% by weight of threonine, 3 to 6% by weight of serine, 10 to 16% by weight of glutamic acid, trace to 8% by weight of proline, 6 to 10% weight of glycine, 6 to 13% by weight of alanine, trace of cysteine, 5 to 12% by weight of valine, trace to 4% by weight of methionine, trace to 3% by weight of cystathionine, 3 to 8% by weight of isoleucine, 8 to 13% by weight of leucine, trace to 5% by weight of tyrosine, 3 to 9% by weight of phenylalanine, trace to 1% by weight of tryptophan, trace to 2% by weight of ornithine, 1 to 4% by weight of lysine, trace to 2% by weight of histidine and 1 to 4% by weight of arginine.

5. A nucleic acid-containing glycoprotein according to claim 1, wherein the saccharide moiety thereof consists of 0.5 to 4.0% by weight of fucose, trace to 2.0% by weight of ribose, 0.3 to 6.0% by weight of arabinose, 2.0 to 40.0% by weight of xylose, 5.0 to 20.0% by weight of mannose, 0.5 to 8.0% by weight of galactose, 30.0 to 80.0% by weight of glucose and trace to 3.0% by weight of glucosamine.

* * * * *